United States Patent
Yousef et al.

(10) Patent No.: US 8,299,020 B2
(45) Date of Patent: Oct. 30, 2012

(54) ANTIMICROBIAL PEPTIDES AND METHODS OF THEIR USE

(75) Inventors: Ahmed El-Meleigy Yousef, Columbus, OH (US); Zengguo He, Columbus, OH (US); Chunhua Yuan, Columbus, OH (US); Liwen Zhang, Delaware, OH (US); Duygu Kisla, Izmir (TR)

(73) Assignee: The Ohio State University Research Foundation, Columbus, OH (US)

( * ) Notice: Subject to any disclaimer, the term of this patent is extended or adjusted under 35 U.S.C. 154(b) by 537 days.

(21) Appl. No.: 12/443,609

(22) PCT Filed: Sep. 28, 2007

(86) PCT No.: PCT/US2007/080016
§ 371 (c)(1),
(2), (4) Date: Mar. 30, 2009

(87) PCT Pub. No.: WO2008/091416
PCT Pub. Date: Jul. 31, 2008

(65) Prior Publication Data
US 2011/0245152 A1    Oct. 6, 2011

Related U.S. Application Data

(60) Provisional application No. 60/827,397, filed on Sep. 28, 2006, provisional application No. 60/827,399, filed on Sep. 28, 2006.

(51) Int. Cl.
| | |
|---|---|
| A01N 37/18 | (2006.01) |
| A61P 31/04 | (2006.01) |
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. ............ 514/2.6; 514/2.4; 514/2.7; 530/324
(58) Field of Classification Search ........................ None
See application file for complete search history.

(56) References Cited

U.S. PATENT DOCUMENTS

| | | |
|---|---|---|
| 6,602,500 B1 | 8/2003 | Kharbanda et al. |
| 6,989,370 B2 | 1/2006 | Stern et al. |
| 7,071,293 B1 | 7/2006 | Tack et al. |
| 2002/0176910 A1 | 11/2002 | Raczek |

FOREIGN PATENT DOCUMENTS

| | | | |
|---|---|---|---|
| WO | WO2005/019250 | * | 3/2005 |
| WO | 2006/016558 | | 2/2006 |

OTHER PUBLICATIONS

Bax, A., and Summers, M.F., J. Am. Chem. Soc., vol. 108(8), pp. 2093-2094, 1986.
Bothner-By, A.A., et al., J. Am. Chem. Soc., vol. 106(3), pp. 811-813, 1984.
Cavanagh, J. and M. Rance, J. Magn Reson., vol. 88, pp. 72-85, 1990.
Chan, W.C. et al., FEBS Left., vol. 252(1), 29-36, 1989.
Cornwell, G.G. et al., Biochem. Biophys. Res. Commun., vol. 154, pp. 648-653, 1988.
E.K. Kelenkamp, M.B., et al., Febs Left., vol. 579(9), pp. 1917-1922, 2005.
Jeener, J. et al., J. Chem. Phys., vol. 71(11), pp. 4546-4553, 1979.
Jung G., Angew. Chem. Int. ed. Eng, vol. 30, pp. 1051-1192, 1991.
Kaletunc, G. J. et al., Appl. Environ. Microbiol., vol. 70, pp. 1116-1122, 2004.
Kay, L.E., et al., J. Am. Chem. Soc., vol. 114(26), pp. 10663-10665, 1992.
Linden, P.K. et al., Clin Infect. Dis., vol. 37, pp. 154-160, 2003.
Martin et al., Biochemistry, vol. 43, pp. 3049-3056, 2004.
Mori, S.A.C., et al., J. Magn Reson., vol. B108, pp. 94-98, 1995.
Rance, M. et al., Biochem. Biophys. Res. Commun., vol. 117(2), pp. 479-485, 1983.
Shaka, a.J. et al., J. Magn Reson., vol. 77(2), pp. 274-293, 1988.
Sklenar, V. et al., J. Magn Reson., vol. A102, pp. 241-245, 1993.
Stackebrandt, E., and B.M. Goebel, Int J. Syst. Bacteriol., vol. 44, pp. 846-849, 1994.
Tankovic, J. et al., J. Clin. Microbiol., vol. 32, pp. 2677-2681, 1994.
Van de Kamp, M. et al., Eur J. Biochem., vol. 230, pp. 587-600, 1995.
Van de Kamp, M. et al., Eur J. Biochem., vol. 227, pp. 757-771, 1995.
Van de Ven, F.J., and Jung, G., Antoine Van Leeuwenhoeek, vol. 69(2), pp. 99-107, 1996.
Wescombe, P.A. And J.R. Tagg, Appl. Environ. Microbiol., vol. 69, pp. 2737-2747, 2003.
Whitford, M.F. et al., Appl. Environ. Microbiol., vol. 67, pp. 569-574, 2001.
Wishart, D.S. et al., J. Biomol. NMR, vol. 6(2), pp. 135-140, 1995.
Wishart, D.S. et al., J. Biomol. NMR, vol. 5(1), pp. 67-81, 1995.
Piuru et al., "A Novel Antimicrobial Activity of a *Paenibacillus polymyxa* strain Isolated from Regional Fermented Sausages", Letters in Applied Microbiology, vol., 27, p. 9713—entire article, esp. introduction, Results, Table 1, 1998.
United States Patent Office Action for U.S. Appl. No. 12/489,820 dated Mar. 26, 2012 (9 pages).
Piuri et al., Letters in Applied Microbiology, 1998, vol. 27, p. 9-13.

* cited by examiner

*Primary Examiner* — Marcela M Cordero Garcia
(74) *Attorney, Agent, or Firm* — Michael Best & Friedrich LLP

(57) ABSTRACT

The present invention relates to a novel *Paenibacillus polymyxa* strain, OSY-DF, and its bioactive mutants. Also provided is a method for using a novel antimicrobial peptide, paenibacillin, isolated from the bacterial strain OSY-DF, and its bioactive variants or fragments. The invention also relates to antimicrobial compositions containing same and methods of their use.

19 Claims, 21 Drawing Sheets

Fig 9:
MS/MS fragments of compound A

| Fragment detected (series 1) | Matched sequence | Fragment detected (series 2) | Matched sequence | Fragment detected (series 3) | Matched sequence |
|---|---|---|---|---|---|
| 202.14 | | 442.34 | | 227.21 | |
| 302.21 | $Dab_5$ | 542.41 | $Dab_5$ | 327.27 | $Dab_8$ |
| 402.28 | $Dab_4$ | 643.45 | $Thr_6$ | 427.33 | $Dab_7$ |
| 503.33 | $Thr_3$ | 743.51 | $Dab_7$ | 528.39 | $Thr_6$ |
| 603.40 | $Dab_2$ | 843.60 | $Dab_8$ | 628.46 | $Dab_5$ |
| | | 1069.78 | $Leu_9\text{-}Leu_{10}$ | 728.53 | $Dab_4$ |
| | | 1169.82 | $Dab_{11}$ | 829.59 | $Thr_3$ |
| | | | | 929.65 | $Dab_2$ |

$$R_1\text{-}Dab_2\text{-}Thr_3\text{-}Dab_4\text{-}Dab_5 \Big\langle \begin{array}{l} Dab_{11}\text{-}Leu_{10}\text{-}Leu_9 \\ \phantom{Dab_{11}\text{-}Leu_{10}\text{-}}| \\ Thr_6\text{-}Dab_7\text{-}Dab_8 \end{array}$$

R1=6-methyloctanoyl

The theoretical molecular weight of polymyxin was calculated as 1168.7656 Da while the measured value was 1168.67 Da (Figure 3). Three fragments series were detected and they all matched partial sequence of Polymyxin E1. Therefore, compound A was identified as Polymyxin E1.

Figure 10
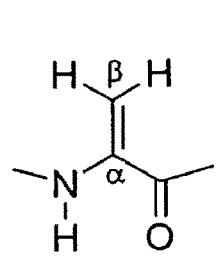
Dha
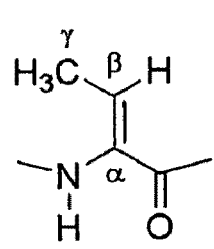
Dhb
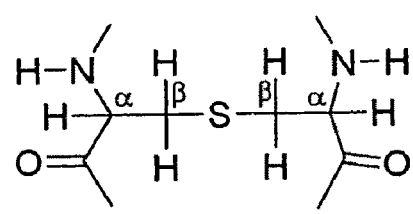
Lanthionine
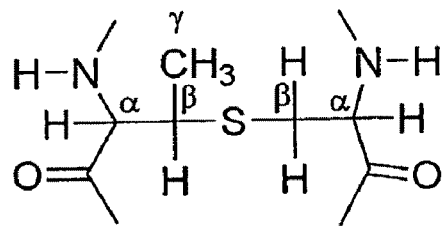
Methyl-Lanthionine
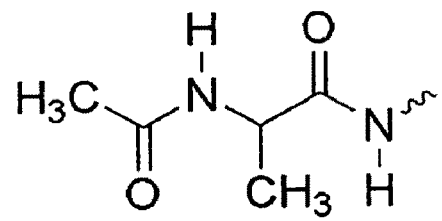
N-acetylation Paenibacillin sequence

US 8,299,020 B2

ANTIMICROBIAL PEPTIDES AND METHODS OF THEIR USE

RELATED APPLICATIONS

This application is a 35 U.S.C. 371 National Phase Application of International Application Serial No. PCT/US07/080016, filed Sep. 28, 2007 for "Antibiotic Antimicrobial Agents and Methods of Their Use," which claims priority to U.S. provisional application No. 60/827,397, filed Sep. 28, 2006, and 60/827,399, also filed Sep. 28, 2006, the entire contents of which are incorporated herein by reference.

BACKGROUND

The emergence of bacterial antibiotic resistance has mobilized the search for new potent antimicrobial agents. Although much of the resistance was observed in hospital environments and related nosocomial infections, there is increasing evidence that resistant food-borne pathogens evolved due to antibiotic use in animal feed. Antimicrobial resistance phenotypes have been recognized in many zoonotic food-transmitted pathogens, including *Salmonella* spp., *Campylobacter* spp., *Listeria* spp., *Escherichia coli* O157:H7, and *Yersinia* spp. Consequently, there is a strong need for new antimicrobials that have suitable pharmacokinetic properties and safety profiles, with activity against these resistant pathogens. Similarly, antimicrobials of natural sources are needed for pharmaceutical, food, feed, and agricultural applications. To this end, considerable efforts have been directed at the search and isolation of new strains of bacteria and new active products of natural origin such as antimicrobial peptides (AMP).

Natural AMP are ribosomally-synthesized peptides that are produced by many species ranging from bacteria to humans. Most AMP are positively charged and contain 20 to 50 amino acid residues in length. Among AMP family is a distinct class of lanthionine (Lan)/β-methyllanthionine (MeLan)-containing peptides, termed lantibiotics.

Lantibiotics are group I bacteriocins that are synthesized and post-translationally modified by Gram-positive bacteria. These modifications generate dehydrated amino acids, i.e., α,β-didehydroalanine (Dha) and α,β-didehydrobutyric acid (Dhb) and thioether bridges of lanthionine (Lan) and β-methyllanthionine (MeLan), as well as some other less frequently encountered modifications. These modified residues are believed to stabilize molecular conformations that are essential for the antimicrobial activity of lantibiotics and their resistance to proteases of the producing strains.

Lantibiotics exhibit bactericidal activity against Gram-positive bacteria, other than the producer, generally by forming pores in cell membrane resulting in efflux of cellular components. Pores are generally formed when lantibiotics bind unspecifically to bacteria cell membrane, a wide-spread property among AMPS. However, some lantibiotics specifically target Lipid II, the precursor in cell wall synthesis, leading to pore formation. It appears more unfavorable for microbes to develop resistance to lipid II-targeting lantibiotics, compared to developing resistance to antibiotics that target a single enzyme involved in cell wall assembly. Altering a biosynthetic intermediate such as lipid II is much more challenging to targeted cells than modifying the structure of an enzyme. For example, in several cases (e.g., nisin) the lantibiotics binding site in lipid II is a motif distinctly different from the vacomycin's binding site. Due to these unique features, some lantibiotics are potent against multi-resistant and vancomycin-resistant bacterial strains.

The lantibiotics produced by lactic acid bacteria have been tested as biopreservatives in a number of food products, with nisin being the most prominent member of these bacteriocins. For decades, nisin has been used worldwide as a food additive, and it is the only lantibiotic approved by the World Health Organization as a food preservative. However, the solubility and efficacy of nisin are highly pH dependent; therefore, the bacteriocin is only useful as a preservative in acidic foods. In addition, nisin is generally inactive against Gram-negative bacteria, imposing a limitation on its usage against important food-borne pathogens, such as *E. coli*, *Salmonella* spp., *Campylobacter* spp., and *Yersinia* spp. In fact, bacteriocins with activity against Gram-negative bacteria are scarcely reported. Similarly, in spite of their antimicrobial potency, previous lantibiotics have had limited clinical applications, largely because of their poor pharmacokinetic properties.

Thus, screening for new effective lantibiotics with potentially favorable pharmacokinetic properties, as well as novel microbial strains with potent antimicrobial activity is needed.

SUMMARY

The present invention relates to a novel *Paenibacillus polymyxa* strain, OSY-DF, and its bioactive mutants. Also provided is a method for using a novel antimicrobial peptide, paenibacillin, isolated from the bacterial strain OSY-DF, and its bioactive variants and fragments.

Accordingly, one embodiment of the invention is directed to an isolated *Paenibacillus polymyxa*, strain OSY-DF, registered under accession no. ATCC PTA-7852, and mutants thereof.

Another embodiment is directed to a bacterial composition containing the *Paenibacillus polymyxa* strain OSY-DF, a fermentate or crude extract of a live culture of *Paenibacillus polymyxa*, strain OSY-DF, or a live culture of a bioactive mutant thereof.

Accordingly, one embodiment is directed to a method of treating a subject against bacterial infection or colonization, including administering to the subject an effective amount of a bacterial composition of the invention. The bacterial infection may be with one or more Gram-positive and/or Gram-negative bacteria.

Another embodiment is directed to a method for inhibiting the growth or colonization of bacteria on or inside an environment, by introducing onto one or more surfaces of the environment an effective amount of a bacterial composition of the invention.

In another aspect, the invention is also directed to one or more isolated peptides having an amino acid sequence that is at least 80%, 90% or 100% identical with the sequence: I. X-A-S-I-I-K-T-T-I-K-V-S-K-A-V-C-K-T-L-T-C-I-C-T-G-S-C-S-N-C-K (SEQ ID NO: 1); II. X-A-S-I-I-K-T-T-I-K-V-S-K-A-V-C-K-T-L-T-C-I-C-T-G-C-C-S-N-S-K (SEQ ID NO: 2); III. X-A-S-I-I-K-T-T-I-K-V-C-K-A-V-S-K-T-L-T-C-I-C-T-G-S-C-S-N-C-K (SEQ ID NO: 3); or IV. X-A-S-I-I-K-T-T-I-K-V-C-K-A-V-S-K-T-L-T-C-I-C-T-G-C-C-S-N-S-K (SEQ ID NO: 4); wherein the peptide is a lantibiotic.

In some embodiments, the isolated peptides have one or more of the following modifications: (i) a thioether bridge of lanthionine (Lan) between the amino acids in positions 11 and 15, and/or positions 25 and 29; (ii) a thioether bridge of β-methyllanthionine (MeLan between a pair of amino acids in positions 17 and 20, a pair in positions 19 and 22, and a pair in positions 23 and 26; (iii) an acetylated amino acid in the N-terminal; (iv) dehydration of one or more serines to dehydro-alanine (Dha); (v) dehydration of one or more threonines to dehydro-butyrine (Dhb); (vi) a Dhb-Dhb tandem, or a combination thereof.

In one embodiment, the isolated peptide has the sequence and the modifications depicted in FIG. 20.

In one embodiment, one or more peptides of the invention are produced by a *Paenibacillus polymyxa*. In one embodiment, the *Paenibacillus polymyxa* producing the peptides is strain OSY-DF, registered under accession no. ATCC PTA-7852.

Accordingly, one embodiment is directed to peptide compositions containing the isolated peptides of the invention.

Another embodiment is directed to a method of treating a subject against bacterial infection or colonization, including administering to the subject an effective amount of a peptide composition of the invention.

Another embodiment is directed to a method for preventing or inhibiting the growth of bacteria on or inside an environment, including introducing onto one or more surfaces of the environment an effective amount of a peptide composition of the invention.

The invention is also directed to methods of producing a paenibacillin peptide, or a bioactive variant or fragment thereof. Such a method includes: providing a microorganism, other than the *Paenibacillus polymyxa* strain OSY-DF, wherein the microorganism includes a polynucleotide encoding the paenibacillin peptide, or a bioactive variant or fragment thereof, and a promoter operably linked to the polynucleotide. Using this method, the paenibacillin peptide, or the bioactive variant or fragment thereof, can be produced by the non-OSY-DF microorganism.

The invention is also directed at a method for inhibiting the growth or activity of susceptible bacteria in an environment. Such a method includes: (A) providing a microorganism, other than the *Paenibacillus polymyxa* strain OSY-DF, wherein the microorganism includes a polynucleotide encoding the paenibacillin peptide, or a bioactive variant or fragment thereof, and a promoter operably linked to the polynucleotide; and (B) applying the microorganism to the environment in an amount sufficient to inhibit the growth of susceptible bacteria.

BRIEF DESCRIPTION OF THE DRAWINGS

FIG. 9. MS/MS fragments of compound A (Figure discloses SEQ ID NO: 10).

FIG. 10. Modified residues found in paenibacillin.

FIG. 12 1D $^1$H NMR recorded in $D_2O$ showing the characteristic peaks attributed to Dha and Dhb. No other downfield peaks (>6.8 ppm) were observed, indicating the absence of aromatic residues. The peak integrations of "I1" and "I2" are corresponding to the spins of $H^\beta$/V14 and "Me+$H^\beta$/I21", respectively. It is deduced from the ratio that $\overline{Me}$ is a methyl group.

DETAILED DESCRIPTION

Figure 1:
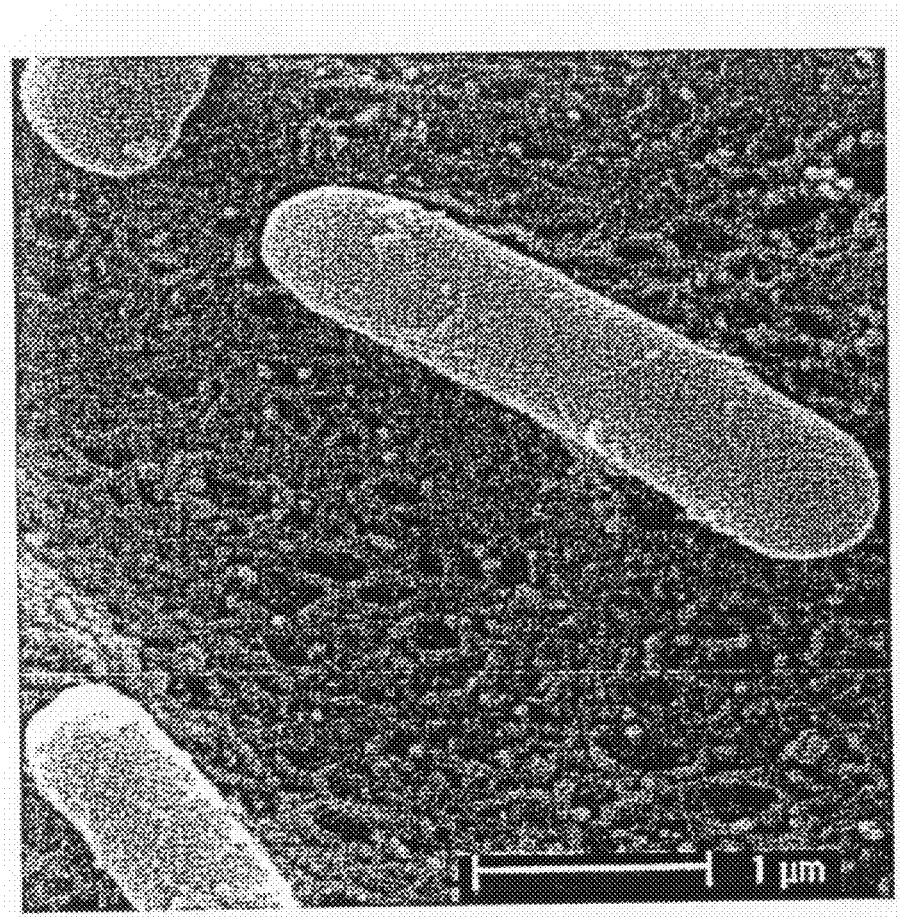
FIG. 1. Scanning electron microscope observation of *Paenibacillus polymyxa* OSY-DF.

Provided is a novel *Paenibacillus polymyxa* strain, referred to herein as OSY-DF, its bioactive mutants. Also provided is a novel antimicrobial peptide isolated from the bacterial strain OSY-DF, referred to herein as paenibacillin, bioactive variants or fragments thereof. The invention also relates to compositions containing same and methods of their use.

The invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

I. Isolated Bacterial Strain

One aspect of the present invention relates to an isolated *Paenibacillus polymyxa* bacterial strain OSY-DF, which has been deposited with the American Type Culture Collection (ATCC), Manassas, Va., on Sep. 1, 2006 and assigned Accession Number PTA-7852. The culture of OSY-DF strain has an inhibitory affect on various Gram-positive and Gram-negative acteria.

The OSY-DF strain was isolated from a fermented food, kimchee, a traditional Korea food consumed for hundreds of years with no apparent health hazards. The strain OSY-DF is a hardy bacterium that survives adverse environmental conditions such as extreme temperatures, drying, acidity and lack of nutrients. These features render the strain a good candidate for incorporation into antimicrobial formulations. Live cultures of *Paenibacillus polymyxa* strain OSY-DF, fermentates derived from these cultures, or their crude extracts are useful in various applications.

One feature of the OSY-DF strain is its easy production of two antimicrobial agents in situ, namely: (i) Polymyxin E1, which is a known antibiotic active against Gram-negative bacteria, like *Escherichia coli* 0157, *Pseudomonas* spp., *Salmonella enterica serovars*, and *Yersinia enterocolitica*, and other Gram-negative bacteria, and (ii) a lantibiotic (paenibacillin) which is active against a broad range of Gram-positive pathogenic and spoilage bacteria, including *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae*. The OSY-DF strain produces these antimicrobial agents in rich or minimal media and in liquid or solid cultures.

An "isolated" or "purified" bacterial strain is substantially free of materials from its natural environment. The language "substantially free of materials from its natural environment" includes preparations or cultures of the bacterium in which the bacterium is separated from components of the environment in which it is naturally found. In one embodiment, the language "substantially free of materials from its natural environment" includes cultures having less than about 20% (by count) of non-OSY-DF bacteria (also referred to herein as contaminating bacteria, contaminating bacteria does not include bioactive mutants or modified forms of strain OSY-DF), or cultures having less than 10% (by count) of non-OSY-DF bacteria, or cultures having less than about 5% non-OSY-DF bacteria.

Provided here are bioactive mutants or modified forms of strain OSY-DF that retain their ability to produce a paenibacillin, or a bioactive variant or fragment thereof, which is capable of inhibiting the growth or activity of one or more susceptible Gram-positive bacteria. Examples of susceptible Gram-positive bacteria include, but are not limited to: *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae* or a combination thereof.

In some embodiments, the bioactive mutants are capable of producing polymyxin E1, which is a known antibiotic active against Gram-negative bacteria, like *Escherichia coli* 0157, *Pseudomonas* spp., *Salmonella enterica serovars*, and *Yersinia enterocolitica*, and other Gram-negative bacteria.

As used herein, the term "bioactive mutants" or "modified forms of strain OSY-DF" are used interchangeably and include bacteria which have naturally mutated, or which have been manipulated, for example by chemical or UV mutation or genetic modification or transformation, and so have been modified to have other characteristics such as, for example, antibiotic resistance.

"Susceptible bacteria" refers to bacterial strains that are either killed, or whose growth or activity is inhibited by a particular compound, such as a live culture, fermentate, crude extract, antibiotic, lantibiotic, peptide, antimicrobial agent, or composition of the present invention.

The terms "active against" or "capable of inhibiting the growth or activity of" a bacterial species refers to a compound's ability to kill (i.e., inactivate) or inhibit (i.e., suppress) the growth or activity of a susceptible microorganism. Such an inhibition can be measured, for example, against control systems. Standard assays, such as those described herein, can be used to determine the ability of a compound to act against bacteria of interest. The standard assays can be conducted in vitro or in the field.

The OSY-DF strain, bioactive mutants or modified forms thereof can be in vegetative or spore state. They can be in culture, cell suspension, dried, dead or viable or in any other form.

Also provided is a fermentate of a live culture of *Paenibacillus polymyxa*, strain OSY-DF, registered under accession no. ATCC PTA-7852, or a bioactive mutant or modified form of strain OSY-DF.

"Fermentate" refers to a microorganism plus the medium in which the microorganism (e.g., *P. polymyxa* OSY-DF or its mutant) has grown and secreted its metabolites. The metabolites of interest in the present invention are the antimicrobial agents discussed above. Fermentate refers to the cultured strain (that is after inoculation of strain in a medium and incubation) which includes both the live biomass and the metabolites, i.e. antimicrobial agents.

Such a fermentate may be capable of inhibiting the growth or activity of one or more Gram-positive bacteria, including, but not limited to: *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae* or combinations thereof.

Alternatively, or in addition, the fermentate may be capable of inhibiting the growth or activity of one or more Gram-negative bacteria, including, but not limited to: *Escherichia coli* 0157, *Pseudomonas* spp., *Salmonella enterica serovars*, and *Yersinia enterocolitica*, and other Gram-negative bacteria.

Also provided are crude extracts of a live culture of *Paenibacillus polymyxa*, strain OSY-DF, or a bioactive mutant or modified form of strain OSY-DF.

"Crude extract" is partially purified active antimicrobial agent(s), derived from the fermentate or from the separated cells.

Such a crude extract may be capable of inhibiting the growth or activity of one or more Gram-positive bacteria, including, but not limited to: *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae* and combinations thereof.

Alternatively, or in addition, the crude extract may be capable of inhibiting the growth or activity of one or more Gram-negative bacteria, including, but not limited to: *Escherichia coli* 0157, *Pseudomonas* spp., *Salmonella enterica serovars*, and *Yersinia enterocolitica*, and other Gram-negative bacteria.

II. Bacterial Compositions

Also provided is a method for using the use of a live culture of *Paenibacillus polymyxa* OSY-DF, a live culture of a bioactive mutant of OSY-DF, or a fermentate or crude extract thereof, in various compositions that can be suitable as antimicrobial agents. The production of one or two antimicrobial agents by the OSY-DF strain, and/or its bioactive mutants, makes this strain useful in applications that aim at reducing or eradicating Gram-positive and/or Gram-negative pathogens, or non-pathogenic contaminants, in a targeted environment.

Accordingly, also provided are compositions, hereinafter referred to as "bacterial compositions," containing a live culture of *Paenibacillus polymyxa* OSY-DF, a live culture of a bioactive mutant of OSY-DF, or a fermentate or crude extract of a live culture of *Paenibacillus polymyxa* OSY-DF or its bioactive mutants. Such bacterial compositions are either capable of producing, or already contain, antimicrobial agents that are capable of inhibiting the growth or activity of Gram-positive and/or Gram-native bacteria.

The bacterial compositions of the present invention may be effective against one or more Gram-positive bacterial species. Examples of susceptible Gram-positive bacteria include, but are not limited to: *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae*, or combinations thereof.

Alternatively, or in addition, bacterial compositions of the present invention may be effective against one or more Gram-negative bacterial species. Examples of susceptible Gram-negative bacteria include, but are not limited to: of *Acinetobacter* spp., *Escherichia coli* 0157, *Pseudomonas* spp., *Salmonella enterica serovars*, *Yersinia enterocolitica*, or combinations thereof.

Any of the bacterial compositions of the present invention can be used in any environment where it is desired to reduce or eradicate certain harmful bacteria as further described herein.

III. Isolated Paenibacillin Lantibiotic

Also provides is an isolated "paenibacillin" peptide, and bioactive variants or fragments thereof. It is believed that paenibacillin is the first lantibiotic to be discovered in genus *Paenibacillus*.

The novel lantibiotic peptide "Paenibacillin," also referred to as the "OSY-DF peptide," was first isolated from *Paenibacillus polymyxa* strain OSY-DF, registered under accession no. ATCC PTA-7852, and has the amino acid sequence shown in FIG. 20 (SEQ ID NO: 5). (The chemical shift assignments were deposited in Biological Magnetic Resonance Data Bank (BMRB; http://www.bmrb.wisc.edu) under Accession No. 15489). Paenibacillin also has the following modifications: (i) two thioether bridges of lanthionine (Lan) formed between the amino acids in positions 11 and 15, and positions 25 and 29; (ii) three thioether bridges of β-methyllanthionine (MeLan) formed between the amino acids in positions 17 and 20, positions 19 and 22, and positions 23 and 26; (iii) an acetylated amino acid in the N-terminal; (iv) two dehydrated amino acids α,β-didehydroalanine (Dha); (v) two dehydrated amino acids α,β-didehydrbutyric acid (Dhb); (vi) a Dhb-Dhb tandem.

Paenibacillin exhibits a relatively broad antimicrobial spectrum, showing activity against a panel of Gram-positive bacteria including spore- and nonspore-formers, and pathogenic and spoilage bacteria. This peptide is quite stable at the temperatures tested; it even retained its activity after a short autoclaving. These characteristics suggest the feasibility of using this peptide in preserving a wide range of foods, or in pharmaceutical compositions that require heating during preparation. Unlike nisin, which is stable at low pH (pH 2.0) but loses activity sharply in the neutral pH region, paenibacillin is quite stable at a wide pH range, from 2.0 to 9.0. Thus, the paenibacillin is stable from a pH of 2, 3, 4, 5, 6, 7, 8, and 9 and increments therebetween from 0.1, 0.2, 0.3, 0.4, 0.5, 0.6, 0.7, 0.8 and 0.9. The new peptide is also easy to dissolve in water, and it has multiple positively-charged residues (no less than 4 Lys). These features may influence the potency and flexibility of OSY-DF peptide paenibacillin such that is it suitable for use in formulations useful in a variety of applications and environments.

The invention also encompasses bioactive variants or fragments of paenibacillin. The term "bioactive variant" is used to refer to a peptide which is a variant of paenibacillin having an amino acid sequence that is at least about 80, 81, 82, 83, 84, 85, 86, 87, 88, 89, 90, 91, 92, 93, 94, 95, 96, 97, 98, 99, or higher percent, identical to the sequence in FIG. 20 (BMRB Accession No. 15489) (SEQ ID NO: 5), prior to dehydration of serine to dehydro-alanine (Dha) and threonine to dehydrobutyrine (Dhb) and formation of thioether bridges.

A "variant" peptide has an altered sequence in which one or more of the amino acids in the reference, or native paenibacillin sequence is deleted and/or substituted, and/or one or more amino acids are inserted into the sequence of the reference amino acid sequence. A variant can have any combination of deletions, substitutions, or insertions.

A "bioactive" variant or fragment of paenibacillin has an amino acid sequence sufficiently homologous to the amino acid sequence of paenibacillin, SEQ ID NO: 5, (BMRB Accession No. 15489), so as to maintain the ability to inhibit the growth or activity of one or more Gram-positive bacterial species. In several examples, the Gram-positive bacterial species that are susceptible to bioactive variants or fragments are selected from the following group: *Bacillus* spp., *Clostridium sporogenes, Lactobacillus* spp., *Lactococcus lactis, Leuconostoc mesenteroides, Listeria* spp., *Pediococcus cerevisiae, Staphylococcus aureus, Streptococcus agalactiae,* or combinations thereof.

In one example, the bioactive variant or fragment has the same amino acids that correspond with as the amino acids of positions 1, 6, 7, 11, 15, 17, 19, 20, 22, 23, 25, 26, and 29 in paenibacillin (SEQ ID NO: 5). In another example, the bioactive variant or fragment of paenibacillin has seven Ala residues and three Abu residues.

In one embodiment, the bioactive variants or fragments may have one or more thioether bridges of lanthionine (Lan). In one example, the Lan bridges are formed between pairs of amino acids in positions 11 and 15, and/or positions 25 and 29.

Alternatively, or in addition to these LAN bridges, the bioactive variants or fragments may have one or more thioether bridge of β-methyllanthionine (MeLan). In one example, the MeLan bridges are formed between pairs of amino acids in positions 17 and 20, positions 19 and 22, and/or positions 23 and 26.

In other embodiments, the bioactive variants or fragments of paenibacillin can have one or more modifications chosen from the group consisting of: an acetylated amino acid in the N-terminal; one or two dehydrated amino acids α,β-didehydroalanine (Dha); one or two dehydrated amino acids α,β-didehydrbutyric acid (Dhb); a Dhb-Dhb tandem, or a combination thereof.

In some embodiments, the bioactive variant comprises a modified sequence of paenibacillin where certain amino acids have been replaced by conservative substitutions. A "conservative substitution" is the replacement of one amino acid by another chemically similar amino acid, which is generally expected to lead to either no change or only a small change in the properties of the peptide. In some examples, such chemically similar amino acids have a similar side chain.

Examples of amino acids that may be modified by conservative substitution include the replacement of one or more Lys residues of paenibacillin with one or more basic, polar amino acids, so that the charge of the bioactive variant is substantially the same as that for paenibacillin.

Alternatively, amino acid residues that do not participate in the Lan and/or Melan bridge formation may be modified by conservative substitution.

In some example, the bioactive variants of paenibacillin peptide comprise a paenibacillin sequence modified in a manner so as to preserve the charge, polarity, C-terminal configuration, N-terminal acetylation, and three dimensional structure of paenibacillin. In some examples, the bioactive variants of paenibacillin peptide comprise a paenibacillin sequence modified in a manner so as to enhance the activity, stability and solubility of the peptide.

An "isolated" or "purified" paenibacillin or bioactive variant or fragment thereof is substantially free of cellular material when produced by extraction from a bacterial system, or chemical precursors or other chemicals when chemically synthesized. In one embodiment, the language "substantially free of cellular material" includes preparations having less than about 30% (by dry weight) of non-OSY-DF peptides or protein (also referred to herein as contaminating protein), less than 20% (by dry weight) of non-OSY-DF peptides or protein, less than about 10% (by dry weight) of non-OSY-DF peptides or protein and/or less than about 5% (by dry weight) of non-OSY-DF peptides or protein. The language "substantially free of chemical precursors or other chemicals" includes preparations of peptides in which the peptides are separated from chemical precursors or other chemicals which are involved in the synthesis of the peptides. In one embodiment, the language "substantially free of chemical precursors or other chemicals" includes preparations having less than about 30% (by dry weight) of chemical precursors or non-OSY-DF chemicals, less than 20% (by dry weight) of chemical precursors or non-OSY-DF chemicals, less than about 10% (by dry weight) of chemical precursors or non-PKB1 chemicals and/or less than about 5% (by dry weight) of chemical precursors or non-OSY-DF chemicals. In some embodiments, isolated OSY-DF lantibiotic or peptides or bioactive fragments thereof are free of contaminating proteins from the same bacteria from which the lantibiotic or peptides are derived. Typically, such lantibiotic and peptides are produced by extraction from the culture of the bacteria which produces them.

It should be noted that paenibacillin or its bioactive variant or fragment may also comprise amino acids linked to either end, or both. These additional sequences may facilitate expression, purification, identification, solubility, membrane transport, stability, activity, localization, toxicity, and/or specificity of the resulting peptide, or it may be added for some other reason. The peptides may be linked directly or via a spacer sequence. The spacer sequence may or may not comprise a protease recognition site to allow for the removal of amino acids. Examples of amino acids that may be linked to paenibacillin, or its bioactive variant or fragment, include, but are not limited to, a polyhistidine tag, maltose-binding protein (MBP), glutathione S-transferase (GST), tandem affinity purification (TAP) tag, calcium modulating protein (calmodulin) tag, covalent yet dissociable (CYD) NorpD peptide, Strep II, FLAG, heavy chain of protein C(HPC) peptide tag, green fluorescent protein (GFP), metal affinity tag (MAT), and/or a herpes simplex virus (HSV) tag. It should be further noted that paenibacillin, or its bioactive variant or fragment, may also comprise non-amino acid tags linked anywhere along sequence. These additional non-amino acid tags may facilitate expression, purification, identification, solubility, membrane transport, stability, activity, localization, toxicity, and/or specificity of the resulting peptide, or it may be added for some other reason. Paenibacillin, or its bioactive variant or fragment, may be linked directly or via a spacer to the non-amino acid tag. Examples of non-amino acid tags include, but are not limited to, biotin, carbohydrate moieties, lipid moieties, fluorescence groups, and/or quenching groups. Paenibacillin, or its bioactive variant or fragment, may or may not require chemical, biological, or some other type of modification in order to facilitate linkage to additional groups.

The invention also provides paenibacillin chimeric or fusion proteins. As used herein, paenibacillin "chimeric" or "fusion" proteins comprise a paenibacillin peptide operatively linked to a non-paenibacillin peptide or protein. A "paenibacillin peptide" is a peptide or bioactive fragment or portion thereof as defined hereinbefore, whereas a "non-paenibacillin peptide or protein refers to a peptide or protein having an amino acid sequence corresponding to a protein which is not substantially homologous to any one of the paenibacillin peptides, e.g. a protein that is different from the paenibacillin peptides and which is derived from the same or a different organism. Within the fusion protein, the term "operatively linked" is intended to indicate that the paenibacillin peptide and the non-paenibacillin peptide or protein are fused in-frame to each other. The non-paenibacillin peptide or protein can be fused to the paenibacillin peptide in any suitable way provided that it does not eliminate the antibiotic function of the peptide. Such fusion or chimeric proteins can be selected to enhance, for example, delivery, handling, purification or effect of the paenibacillin peptide from which it is formed. Fusion or chimeric proteins can be produced by any desired means.

All percentage identities for the amino acid sequences noted above can be determined using a variety of algorithms known in the art. To determine the percent identity of two amino acid sequences, the sequences are aligned for optimal comparison purposes (e.g. gaps can be introduced in the sequence of one sequence for optimal alignment with the other sequence). The amino acid residues at corresponding amino acid positions are then compared. When a position in one sequence is occupied by the same amino acid residue as the corresponding position in the other sequence, then the molecules are identical at that position. The percent identity between the two sequences is a function of the number of identical positions shared by the sequences (i.e. % identity=# of identical positions/total# of positions×100).

The paenibacillin, or bioactive variants or fragments of paenibacillin can be produced by the *Paenibacillus polymyxa* strain OSY-DF, registered under accession no. ATCC PTA-7852, or a bioactive mutant of the OSY-DF strain.

In some embodiments, paenibacillin, or its bioactive variants or fragments can be produced by a microorganism other than the OSY-DF strain. Thus, the invention also relates to a method of producing a paenibacillin peptide, or its bioactive variants or fragments, which includes: providing a microorganism, other than the *Paenibacillus polymyxa* strain OSY-DF, wherein said microorganism contains a polynucleotide encoding the paenibacillin peptide, or a bioactive variant or fragment thereof, and a promoter operably linked to the polynucleotide. The microorganism can then be grown in a suitable fashion so that it produces paenibacillin, or its bioactive variants or fragments.

The polynucleotide can be part of a vector that is heterologous to the microorganism. The vector may include other polynucleotide sequences, such as a second polynucleotide that encodes a paenibacillin peptide-processing-peptide operably linked to said first polynucleotide. In one example, either the peptide(s) encoded by one or both polynucleotides described above is heterologous to the microorganism.

In other embodiments, a bioactive variant or fragment of paenibacillin is produced by modifying the paenibacillin sequence, SEQ ID NO: 5. In one embodiment, the amino acids of Paenibacillin may be suitably modified by one or more conservative substitutions, as described above.

The bioactive variants or fragments of paenibacillin are Type A lantibiotics. The defining characteristic of lantibiotics is that they contain the unusual amino acid lanthionine or β-methyllanthionine, which are formed by posttranslational dehydration of serine or threonine, respectively, followed by a Michael-type nucleophilic addition of a cysteine sulfhydryl across the double bond. Because of this mechanism, the presence of the lanthionine requires that a cell producing it possess the machinery to dehydrate serines and/or threonines in addition to the ability to form the thioether linkage. Type A lantibiotics are characterized by being elongated and cationic with molecular masses ranging from 2,151 to 4,635 Da. The molecular weight of bioactive variants or fragments of paenibacillin can range from 2300 to 3700 Da.

IV. Peptide Compositions

All the peptides of the invention, including paenibacillin, its bioactive variants or fragments, (referred to hereinafter as "peptides of the invention") may be incorporated into compositions suitable for inhibiting the growth or activity of Gram-positive bacteria. Compositions containing the peptides of the invention shall be referred to as "peptide compositions."

The peptide compositions of the present invention may be effective against one or more Gram-positive bacterial species. Examples of susceptible Gram-positive bacteria include, but are not limited to: *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae*, or combinations thereof.

Other useful compositions of the invention can include the peptides of the invention together with another active agent, i.e., another lantibiotic or a known antibiotic. Example of suitable lantibiotics are Nisin and subtilin. The combination of ingredients can be quite effective when applied together to kill or inhibit the growth of bacteria, especially gram-positive bacteria.

V. Uses and Methods

Any of the bacterial or peptide compositions of the present invention can be used in any environment where it is desired to reduce or eradicate certain harmful bacteria. Some examples of such applications include:

(i) A pharmaceutical preparation for the treatment of bacterial infection in a subject;

(ii) A pharmaceutical preparation for the prevention of bacterial infection or colonization in a subject;

(iii) A probiotic preparation for the control of pathogens;

(iv) A control preparation suitable for use in controlling bacterial colonization of an environment.

Because of the stability of the peptides, it is contemplated that the peptide compositions of the invention may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the inhibition of bacterial growth on such a material is desired.

"Treating" or "treatment" of a disease includes: (1) preventing the disease, i.e. causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The terms "environment" and "environment capable of sustaining or supporting microbial growth" are used interchangeably and refer to any environment where microbial growth can occur or where microbes can exist. Examples of such environments include a fluid (such as water, bodily fluids and other liquids), tissue (such as skin, mucosa, internal tissues, etc. of an animal), space, organism, organ, food, food products or food extracts, surface substance, crops, and certain inanimate objects such as soil. It is not necessary that the environment promote the growth of the microbe, only that it permits its subsistence.

"Controlling bacterial colonization" of an environment refers to reducing the overall bacterial count or population in that environment.

A "control preparation" is any preparation capable of controlling, reducing, or eliminating bacterial count or population in an environment.

A "subject" refers to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

In general, the proper dosage of an antimicrobial composition necessary to prevent microbial growth and proliferation depends upon a number of factors including the types of bacteria that might be present, the environment into which the composition is being introduced, and the time that the composition is envisioned to remain in a given area.

It is further contemplated that the antimicrobial compositions of the invention may be used in combination with or to enhance the activity of other antimicrobial agents or antibiotics. Combinations of the bacterial or peptide compositions with other agents may be useful to allow antibiotics to be used at lower doses due to toxicity concerns, to enhance the activity of antibiotics whose efficacy has been reduced or to effectuate a synergism between the components such that the combination is more effective than the sum of the efficacy of either component independently.

Pharmaceutical preparations: The compositions of the present invention may be used in a pharmaceutical preparation suitable for (a) treating a bacterial infection, or (b) preventing a bacterial infection or colonization, in a subject. The compositions can be provided in combination with a pharmaceutically acceptable carrier.

"Pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier. Suitable pharmaceutically acceptable carriers are well known in the art. The processes of producing the pharmaceutical compositions of the invention are well within the ordinary skill of a worker in the art.

Examples of suitable carriers include, but are not limited to, diluents, preservatives, solubilizers, emulsifiers, adjuvants, and/or other carriers. Diluents can include, but are not limited to, buffers such as Tris-HCl, acetate, phosphate. Additives can include, but are not limited to, detergents and solubilizing agents such as Tween 80, Polysorbate 80, etc. Examples of antioxidants include, but are not limited to, ascorbic acid, sodium metabisulfite, etc. Preservatives can include, but are not limited to, for example, Thimersol, benzyl alcohol, etc., and bulking substances such s lactose, mannitol, etc.

The pharmaceutical composition of the present invention can be incorporated into particulate preparation of polymeric compounds such as polyvinylpyrrolidone, polylactic acid, polyglycolic acid, etc., or into liposomes. Liposomal encapsulation includes encapsulation by various polymers. A wide variety of polymeric carriers may be utilized to contain and/or deliver one or more of the pharmaceutical agents discussed above, including for example both biodegradable and non-biodegradable compositions.

Polymeric carriers can be fashioned in a variety of forms, with desired release characteristics and/or with specific desired properties. For example, polymeric carriers may be fashioned to release a therapeutic agent upon exposure to a specific triggering event such as pH by using pH-sensitive polymers. Likewise, polymeric carriers can be fashioned which are temperature sensitive (See for example U.S. Pat. No. 6,989,370).

A wide variety of forms may be fashioned by polymeric carriers, including for example, rod-shaped devices, pellets, slabs, or capsules. Therapeutic agents may be linked by occlusion in the matrices of the polymer, bound by covalent linkages, or encapsulated in microcapsules. Within certain embodiments of the invention, pharmaceutical compositions are provided in non-capsular formulations such as microspheres (ranging from nanometers to micrometers in size), pastes, threads of various size, films and sprays.

The antimicrobial compositions of the present invention may be used alone or in combination for effective therapeutic results.

In one example, in order to reduce the resistance of a microorganism to an antimicrobial agent, as exemplified by reducing the resistance of a bacterium to an antibiotic, or to kill a microorganism or bacterium, one would generally contact the microorganism or bacterium with an effective amount of the antimicrobial agent to inhibit growth or activity of the microorganism or bacterium. The terms "microorganism" and "bacterium" are used for simplicity and it will be understood that the invention is suitable for use against a population of microorganisms, i.e., "bacteria".

In some circumstances, in terms of killing or reducing the resistance of a bacterium, one may want to contact the bacterium with an effective amount of an antibiotic in combination with an amount of an antimicrobial peptide effective to inhibit growth and/or proliferation in the bacterium. In this regard, the bacterial compositions of the present invention may provide such a combined composition. Alternatively, the peptide compositions of the invention may be combined with another suitable antimicrobial agent, such as an antibiotic, lantibiotic, etc.

The microorganism, e.g., bacterium, or population thereof, may be contacted either in vitro or in vivo. Contacting in vivo may be achieved by administering to an animal (including a human patient) that has, or is suspected to have a microbial or bacterial infection, a therapeutically effective amount of pharmacological preparation of the invention, alone or in combination with a therapeutic amount of a pharmacologically acceptable formulation of another antimicrobial agent. The invention may thus be employed to treat both systemic and localized microbial and bacterial infections by introducing the combination of agents into the general circulation or by applying the combination, e.g., topically to a specific site, such as a wound or burn, or to the eye, ear or other site of infection. Examples of preparation and dosage of such pharmaceutical preparations are known in the art and are described, for example, in U.S. Pat. No. 7,071,293 to Tack, et al., the contents of which are incorporated herein by reference.

Such pharmaceutical preparation may also be used to prevent bacterial colonization before the appearance of signs and symptoms of a disease. In this regard, the compositions of the invention have several applications in both the human and animal context and can even be used in a bio-defense program.

Probiotic preparations: Also provided is a method for using a probiotic preparation containing a live culture of *Paenibacillus polymyxa* OSY-DF or its bioactive mutants, or a fermentate of such live cultures. Such probiotic preparations may be sufficiently stable such that the microorganisms are still live or dormant in the compositions at the time of ingestion by a subject, thereby maintaining activity of the microorganism.

The term "probiotic" means a microorganism that exerts beneficial effects on the health of the host. Probiotics are generally live microbial food supplements which beneficially affect the host human or animal by improving its intestinal microbial balance.

The probiotic composition may contain other additives or carriers, such as sweeteners, etc., useful for maintaining the stability of the probiotic component.

The probiotic composition may be of any form that is orally administrable. For example, the composition may be in the form of tablets, capsules, chewing gum or the like. The composition may also be combined with foods or drinks ordinarily consumed by a subject, or by humans.

In one embodiment, the composition is added to a food product, as described below.

Controlling bacterial colonization of an environment: Also provided is a method for using control preparations suitable for use in controlling bacterial colonization of an environment capable of sustaining or supporting microbial growth.

Accordingly, in some embodiments, a bacterial or peptide composition of the invention can be used in a process for reducing the overall bacterial count or population in an environment by applying to the environment an effective amount of the foregoing composition.

One example of an environment includes food products. The term "food" or "food product" encompasses all edible nutritive substances and compositions, including those intended for human consumption as well as pet or other animal consumption, such as pet food animal feed, etc. "Pet food" means a composition that is intended for ingestion by the pet. Pet food compositions may include, without limitation, nutritionally balanced compositions suitable for daily feed, as well as supplements (e.g., treats, edible films) which may or may not be nutritionally balanced.

In practice, the compositions according to the present invention can be applied to a food in combination with one or more sublethal processing treatments such as sublethal heat treatment.

In other embodiments, the compositions of the present invention can be used as food additives, to be used as (a) a control agent against foodborne pathogens, (b) a probiotic for improving the health of human or pet subjects consuming the foods, and/or (c) a starter culture for safer fermented products.

In an additional embodiment, the present invention provides a food product having a reduced live bacterial population as a result of having applied thereon an effective amount of the foregoing bacterial or peptide composition. Examples of methods of using compositions for this purpose are known in the art, and are described, for example, in Stem et al., U.S. Pat. No. 6,989,370.

In some embodiments, the compositions of the present invention can be used as feed additives, to be used as (a) a probiotic agent to improve the health of farm animals and/or (b) a composition for the prevention or treatment of subjectian diseases. Examples of methods of using compositions for this purpose are known in the art, and are described, for example, in Raczek, Nico N., U.S. Pat. Appl. 2002/0176910.

For example, the composition of the present invention can be encapsulated using a polymeric carrier as described above and then added to a feed by any known means of applying it to feed such as for example, by mechanical mixing, spraying, etc.

In some examples, the composition can be mixed with any granular component that is digestable, such as for example, milled maize grain; ground grains such as for example oats, wheat, buckwheat; ground fruits such as for example, pears, etc. The composition is then added to any type of animal feed in amounts effective to either kill, or inhibit the growth or activity of susceptible bacteria. For purposes of the present invention, examples of animal feed include, but are not limited to, green foder, silages, dried green fodder, roots, tubers, fleshy fruits, grains, seeds, brewer's grains, pomace, brewer's yeast, distillation residues, milling byproducts, byproducts of the production of sugar, starch or oil production, and various food wastes. The product can be added to the animal feedstuffs for cattle, poultry, rabbit, pig, or sheep rearing, etc. It can be used mixed with other feed additives for these stock.

In yet other embodiments, the compositions of the present invention can be used as agricultural biocontrol agents to control plant and soil pathogens.

In an additional embodiment, the present invention provides an agricultural crop having a reduced live bacterial population as a result of having applied thereon an effective amount of the foregoing bacterial or peptide composition.

A "biocontrol agent" or composition refers to a composition that includes an effective amount of a bacterial composition of the present invention. The bacterial composition may also include one or more antimicrobial agents produced by the microorganisms. The compositions may be present with one or more other microorganisms that are antagonists against plant pathogens.

An "effective amount" as used in this context means an amount effective for inhibiting plant pathogen development.

"Biocontrol," or "biological control" agents are used interchangeably and refer to microorganisms that exhibit biological activity useful in controlling plant diseases.

The OSY-DF strain or its bioactive mutants offer promise for use as a control preparation or biocontrol agent because OSY-DF is active against many Gram-positive and/or Gram-negative bacteria. Such compositions are relatively inexpensive to mass produce because they are grown in large volume fermenters and require little or no downstream processing other than, in some embodiments, drying.

In an agriculture setting, once a crop has been treated with a biocontrol agent, it may not need to be treated again for several years because the biocontrol agent is a live organism and can sustain itself in the soil environment. In this regard, the OSY-DF strain and/or its bioactive mutants are suitable organisms for use as a biocontrol agent because they form dormant spores which are resistant to heat, drying, chemical treatment, radiation and ultraviolet light exposure. This makes it possible to store dried cells of *Paenibacillus polymyxa* OSY-DF or its bioactive mutants for long periods with little loss of viability. The same-spore forming ability occurs in the soil, making it possible for the introduced OSY-DF strain or its bioactive mutants to survive long periods of dryness or harsh conditions.

Of course in other embodiments the bacterial and polypeptide agents hereof can be used on non-biological or inert surfaces or substrates.

Production of Polymyxin: Also provided is a method for using the use of a live culture of *Paenibacillus polymyxa* OSY-DF, or its bioactive mutant, to produce the antibiotic polymyxin E1. In liquid culture, this strain can easily produce polymyxin E1, with no significant amount of other polymyxins detected.

Polymyxin E1 is known to be active against *Pseudomonas aeruginosa* and *Acinetobacter baumannii*. The compound was commercially released as early as 1959, but was subsequently relegated to second-line antibiotic because of early reports about its potential toxicity. However, new evidence shows that polymyxins, particularly polymyxin E1, have less toxicity than previously thought. Recent emergence of multidrug-resistant Gram-negative pathogens, such as *P. aeruginosa*, *Salmonella* spp., and *Acinetobacter* spp., has become a major clinical problem. Some of these pathogens (e.g., *A. baumannii*, a pathogen causing bloodstream infections in military medical facilities) have developed substantial antimicrobial resistance and the pathogen is only susceptible to polymyxins (Tankovic, J., et al. (1994) *J. Clin. Microbiol.* 32:2677-2681). The scarcity of newly-introduced antibiotics against resistant Gram-negative bacteria, and the recent confirmation of polymyxin safety, have favored the use of this antibiotic in the therapy of multidrug-resistant Gram-negative bacterial infections (see Linden, P. K., et al. (2003) *Clin. Infect. Dis.* 37:154-160). *Paenibacillus polymyxa* OSY-DF copiously produced only one type of polymyxin, thus the strain, or its bioactive mutants, may be used to synthesize polymyxin E1.

In some embodiments, methods are provided for treating a subject against bacterial infection or colonization by administering to the subject an effective amount of a bacterial or peptide composition or a pharmaceutical preparation as described above.

The composition may be administered by any acceptable route: oral, intravenous, intraperitoneal, topical, nasal, anal or vaginal. The dosage range contemplated is 0.01 to 1000 mg/kg body weight in 1-10 divided doses. Examples of suitable dosages are 0.1 to 500 mg/kg body weight in 1-6 divided doses, and/or 1.0 to 250 mg/kg body weight in 1-4 divided doses.

In one example, the method of administration includes contacting an effective amount of the composition with a susceptible bacterial species. Example of this method of administration include topical antimicrobial preparations, mouthwashes, or wound dressings, preparations used for cleaning, disinfection or lavage of skin, mucosal, or internal surfaces.

Also provided are methods of inhibiting the growth, activity or colonization of bacteria on or inside an environment by adding to the environment an effective amount of a bacterial or peptide composition.

The invention will now be described in part with reference to the following non-limiting examples.

EXAMPLES

SUMMARY OF EXAMPLES 1-5: A new bacterial strain, displaying antimicrobial properties against gram-negative and gram-positive pathogenic bacteria, was isolated from food. Based on its phenotypical and biochemical properties as well as its 16S rRNA gene sequence, the bacterium was identified as *Paenibacillus polymyxa* and it was designated as strain OSY-DF. The antimicrobials produced by this strain were isolated from the fermentation broth and subsequently analyzed by liquid chromatography-mass spectrometry. Two antimicrobials were found: a known antibiotic, polymyxin E1, which is active against gram-negative bacteria, and an unknown 2,983-Da compound showing activity against gram-positive bacteria. The latter was purified to homogeneity, and its antimicrobial potency and proteinaceous nature were confirmed. The antimicrobial peptide, designated paenibacillin, is active against a broad range of food-borne pathogenic and spoilage bacteria, including *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, and *Streptococcus agalactiae*. Furthermore, it possesses the physico-chemical properties of a suitable antimicrobial agent in terms of water solubility, thermal resistance, and stability against acid/alkali (pH 2.0 to 9.0) treatment. Edman degradation, mass spectroscopy, and nuclear magnetic resonance were used to sequence native and chemically modified paenibacillin. The peptide was unequivocally characterized as a novel lantibiotic, with a high degree of posttranslational modifications. The co-production of polymyxin E1 and a lantibiotic is a finding that has not been reported earlier.

Example 1

Isolation and Identification of an Antimicrobial-producing Strain from Food

Strain screening. Fermented foods, including vegetables (kimchee, a Koreanstyle fermented vegetable), soybean sauce, and imported cheeses made of raw or pasteurized milk (gorgonzola, le lingot, roquefort, le brovere, and roncal), were purchased from local food stores (Columbus, Ohio) and screened for microorganisms that produce antimicrobial agents. Briefly, food samples were suspended in 0.1% sterile peptone water and homogenized using a blender or a stomacher. The suspensions were serially diluted and passed through a hydrophobic gridmembrane filter with a pore size of 0.45_m (ISO-GRID; Neogen Corporation, Lansing, Mich.). Bacteria and fungi retained on the membranes were grown into colonies by mounting the membranes onto tryptose agar and acidified potato dextrose agar (Difco, BD Diagnostic Systems, Sparks, Md.), respectively, and incubating at 30° C. for 48 h. To rule out any false-positive inhibition caused by acid production, the basal media were supplemented with 0.6% $CaCO_3$. The colony-carrying membranes were then removed and held in reserve in sterile petri dishes at 4° C. The incubated agar plates, left after removing the membranes, were overlaid with a soft agar medium seeded with *Escherichia coli* K-12. The medium consisted of tryptic soy broth supplemented with 0.6% yeast extract (TSBYE) and 0.75% agar. The overlaid plates were incubated at 37° C. for an additional 12 h to manifest inhibition areas. Isolates corresponding to inhibition areas were located on the membrane filter and streaked onto tryptose agar plates. A sample of kimchee yielded a bacterium (OSY-DF) that produces potent antimicrobial agents.

Cultures and media. The isolated bacterial strain, OSY-DF, was propagated on tryptic soy agar supplemented with 0.6% yeast extract (TSAYE) at 30° C. For stock preparation, the culture was cultivated overnight at 30° C. in TSBYE mixed with sterile glycerol (final concentration of 20%) and stored at _80° C. The indicator strains and media used in this study are listed in Table 1.

TABLE 1

Antimicrobial activity of *Paenibacillus polymyxa* OSY-DF broth and purified Paenibacillin.

| Strain[a] | Broth media[b] | Culture supernatant | Paenibacillin |
|---|---|---|---|
| Gram-negative bacteria | | | |
| *Escherichia coli* K12 | TSBYE | + | − |
| *E. coli* 0157:H7 ATCC 43889 | TSBYE | + | − |
| *E. coli* 0157:H7 EDL-933 (mutant) | TSBYE | + | − |
| *E. coli* 0157:H7 EDL-933 (wild type) | TSBYE | + | − |
| *E. coli* 0157:H12 | TSBYE | + | − |
| *Salmonella enterica* serovar Enteritidis | TSBYE | + | − |
| *Pseudomonas putida* | TSBYE | + | − |
| *Salmonella enterica* ser. Typhimurium OSU 228 | TSBYE | + | − |
| *S. enterica* ser. Typhimurium DT 109 | TSBYE | + | − |
| *S. enterica* ser. Typhimurium FM 12501-51 | TSBYE | + | − |
| *Yersinia enterocolitica* OSU 602 | TSBYE | + | − |
| Gram-positive bacteria | | | |
| *Bacillus cereus* ATCC 14579 | TSBYE | + | + |
| *B. subtilis* ATCC 6633 | TSBYE | + | + |
| *Clostridium sporogenes* OSU 392 | TSBYE | + | + |
| *Lactobacillus acidophilus* ATCC 19992 | MRS | + | + |
| *Lb. casei* ATCC 7469 | MRS | + | + |
| *Lb. plantarum* ATCC 8014 | MRS | + | + |
| *Lactococcus lactis* ATCC 11454 | MRS | + | + |
| *Leuconostoc mesenteroides* | MRS | + | + |
| *Listeria innocua* ATCC 33090 | TSBYE | + | + |
| *L. monocytogenes* OSY-8578 | TSBYE | + | + |
| *L. monocytogenes* Scott A | TSBYE | + | + |
| *Pediococcus cerevisiae* | MRS | + | + |
| *Staphylococcus aureus* | TSBYE | + | + |
| *Streptococcus agalactiae* OSU 602 | TSBYE | + | + |

[a]Strains obtained from the culture collection of the Ohio State University food safety laboratory.
[b]TSBYE, Tryptic soy broth supplemented with yeast extract; MRS, *Lactobacilli* MRS broth.

Phenotypic and biochemical characterizations of the OSY-DF isolate. The morphological characteristics of OSY-DF were observed by Gram staining, spore staining, and scanning electron microscopy examination. For scanning electron microscopy observation, the strain was grown on TSAYE at 30° C. for 48 h. The resulting colonies, on the plate, were fixed with 3.0% glutaraldehyde (vol/vol) in 0.1 M phosphate buffer (pH 7.4) for 3.5 h. Subsequently, the agar surface was rinsed three times (15 min each) with the same buffer to remove traces of glutaraldehyde fixative. The agar area carrying bacteria was excised, postfixed, and dehydrated following a procedure described in Kaletunc G., J. et al. (2004). *Appl. Environ. Microbiol.* 70:1116-1122.

Bacterial cells were sputter coated with gold-palladium and examined in a scanning electron microscope at 30 kV (Philips XL-30; FEI, Inc., Hillsboro, Oreg.). Analyses for the biochemical properties of OSY-DF included catalase, oxidase, and urease reactions, nitrate reduction, gelatin liquefaction, starch hydrolysis, glucose fermentation, esculin hydrolysis, indole production, and H2S formation. In addition, the carbohydrate fermentation pattern of the OSY-DF isolate was determined using a biochemical test kit (API 50CH strips and API CHB/E medium; BioMerieux, Inc., Durham, N.C.). The results were checked after incubating OSY-DF at 30° C. for 24 and 48 h, and the identification was done by referring to the database provided by the kit manufacturer.

16S rRNA gene amplification, cloning, and sequencing. Genomic DNA of the OSY-DF isolate was prepared by suspending two to three colonies from a 24-h culture on TSAYE in 100 µl double-distilled water and boiling for 20 min. A pair of high-performance liquid chromatography (HPLC)-grade universal primers specific for bacterial 16S rRNA, fD1 and rD1 (42), were used to amplify the corresponding gene. Amplification by PCR involved using a Taq DNA polymerase kit (QIAGEN, Valencia, Calif.) under the following conditions: after an initial 3-min incubation at 95° C., the mixture was subjected to 30 cycles, each including 1 min at 95° C., 30 s at 52° C., and 2 min at 72° C. A final extension was performed at 72° C. for 10 min. The amplified 16S rRNA was purified using a commercial DNA extraction kit (QIAquick® gel extraction kit; QIAGEN), ligated to pGEM-T Easy vector (Promega Corporation, Madison, Wis.), and transformed into *E. coli* DH5__ cells via electroporation. The recombinant plasmid was harvested from a 5-ml overnight culture in LB medium using silica spin columns (QIAprep Spin Miniprep kit; QIAGEN) and sequenced (3730 DNA Analyzer; Applied Biosystems, Foster City, Calif.) using T7 terminator and SP6 promoter primers. The derived 16S rRNA gene sequence (~1.5 kb) was compared to known bacterial sequences in the NCBI GenBank using BLAST. Only results from the highest score queries were considered for phylotype identification, with 98% minimum similarity (see Stackebrandt, E., and B. M. Goebel. (1994) *Int. J. Syst. Bacteriol.* 44:846-849).

RESULTS—By applying a convenient hydrophobic grid-membrane-based method, a large number of food isolates were screened for antimicrobial activity against *E. coli* K-12. An isolate from kimchee (pH 4.05) showed a distinct inhibition area on basal tryptose agar. Culture supernatant of this isolate was active against several gram-positive and gram-negative bacteria (Table 1). This isolate formed pale colonies on TSAYE. Morphologically, the isolate was rod shaped, 0.6 by 3.0 μm (FIG. 1), gram-positive bacterium. The cell was motile with peritrichous flagella (data not shown). Upon prolonged incubation on agar medium, cells produced central endospores.

The isolate is positive for catalase, nitrate reduction, gelatin liquefaction, starch hydrolyzation, glucose fermentation, and esculin hydrolysis but negative for oxidase, urease, indole production, and $H_2S$ formation. The bacterium grew well in TSBYE and MRS broth under aerobic conditions. The isolate grew in medium supplemented with ethanol as the sole carbon source, and it further oxidized ethanol to acetic acid in a medium containing 7% ethanol (data not shown). Genomic analysis showed the 16S rRNA gene of the isolate shares >99.0% sequence similarity with that of *Paenibacillus polymyxa*. Carbohydrate fermentation analysis (Api 50 CH kit) confirmed the high similarity of the isolate (>99%) with *P. polymyxa*. Thus, it was concluded that the isolate belongs to *P. polymyxa*, and it was given the strain designation OSY-DF.

Example 2

Antimicrobial Spectrum of *P. polymyxa* OSY-DF Culture Supernatant

Isolation of antimicrobial agents from fermentation broth. A single colony of OSY-DF was subcultured into 10 ml TSBYE and incubated at 30° C. for 24 h. The resulting culture was used to inoculate a 2-liter flask containing 500 ml TSBYE. The flask was incubated at 30° C. for 24 h in a rotary shaker (New Brunswick Scientific, Edison, N.J.) with agitation at 195 rpm. Cells in the fermentation broth were separated by centrifugation at 12,000×g for 20 min. The resulting cell-free supernatant was g-filtered (0.45-μm-pore-size filter; Millipore) and mixed with Amberlite XAD-7 resin (Sigma, St. Louis, Mo.) at a 10% level, and the mixture was maintained at 4° C. for 24 h with stirring to allow maximum adsorption. The resin, with adsorbed antimicrobials, was collected by filtration and washed sequentially with 2 liters distilled water and 1 liter 30% (vol/vol) ethanol. The resin was re-suspended in 250 ml ethanol (75% vol/vol; pH 2.0) and maintained at 25° C. for 4 h with agitation followed by filtration. The resulting ethanol fraction, which contained the antimicrobial agents, was condensed by a rotary evaporator at 35° C. under vacuum, and the concentrate was freeze dried. The generated powder (approximately 0.5 g) was reconstituted in 5 ml distilled water followed by centrifugation. The resulting supernatant, herein referred to as the antimicrobial crude extract (CE), contained $2 \times 10^5$ arbitrary units (AU)/ml as determined by the bioassay method described below.

Antimicrobial activity determination. A qualitative and quantitative bioassay for antimicrobial potency was done using the spot-on-lawn method. An indicator lawn was prepared by pouring 10 ml soft agar (seeded with 200 μl overnight indicator culture) onto tryptose agar as a basal medium, in a petri dish. *Escherichia coli* K-12 and *Lactobacillus plantarum* ATCC 8014 were generally used as the gram-negative and gram-positive sensitive indicators, respectively, but other bacteria were tested to determine the OSY-DF antimicrobial spectrum (Table 1). For qualitative tests, aliquots (10 μl) of cell-free culture supernatant (pH 6.5) were spotted on indicator lawns, and the plates were incubated overnight for inhibition area observation. A clear inhibition area of $\geq 3$ mm in diameter was recorded as positive. For the quantitative measurements, the cell-free culture supernatant was twofold serially diluted and dilutions were spotted onto the indicator lawn as just described. Antimicrobial activity was expressed in AU/ml; these values are the reciprocal of the highest dilution displaying a clear zone of inhibition that corresponds to 1 ml of the nondiluted supernatant.

RESULTS—When tested against a panel of gram-negative and gram-positive bacteria, OSY-DF cell-free culture supernatant (CFCS) and crude extract (CE) exhibited a broad spectrum of antimicrobial activity. All pathogenic bacteria tested in this study were sensitive to the CFCS and CE of OSY-DF; these are *Escherichia coli* 0157:H7 (three strains), *Salmonella enterica* serovar Enteritidis, *S. enterica* serovar Typhimurium (four strains, including the multidrug-resistant DT109 and FM 12501-51), *Yersinia enterocolitica*, *Bacillus cereus*, *Listeria monocytogenes* (three strains, including the processing-resistant OSY-8578), and *Staphylococcus aureus* (Table 1). However, the CFCS and CE of OSY-DF had no activity against fungi (data not shown).

Example 3

Isolation, Purification, and Characterization of Antibacterial Substances produced by *P. polymyxa* OSY-DF Separation and purification by HPLC of the OSY-DF peptide. The HPLC system consisted of a pump (model SP8800; Thermo Separation Products, Fremont, Calif.), UV-Vis monitor (model 1706; Bio-Rad Laboratories, Milford, Mass.), and an integrator (HP 3396 series III; Hewlett-Packard). Separation was achieved using an ether-linked phenyl-based reversed-phase, 250-by 2.0-mm column with 4-μm particle size (Phenomenex Synergi; Phenomenex, Torrance, Calif.). The mobile phase consisted of (i) methanol and (ii) HPLC-grade water containing 0.1% trifluoroacetic acid (TFA). A 30 μl aliquot of CE was loaded and separated on the column by a linear biphasic gradient of 20 to 40% methanol over 10 min (2% methanol/min), 40 to 60% over 5 min (4% methanol/min), and 60 to 70% over 10 min (1% methanol/min) at a flow rate of 0.3 mL/min. Elution was monitored at a wavelength of 220 nm, and fractions were collected manually for the antimicrobial activity bioassay. Fractions that exhibited antimicrobial activity, at a given retention time, were collected from different HPLC runs, pooled, and lyophilized. Powder from pooled anti-gram-positive fractions was reconstituted and repurified using the same HPLC conditions described earlier. Collected fractions from multiple HPLC runs were lyophilized again, and the resulting powder was checked for efficacy against gram-positive bacteria. The antimicrobial agent in this powder will be referred to as the OSY-DF peptide.

SDS-PAGE. Sodium dodecyl sulfate-polyacrylamide gel electrophoresis (SDSPAGE) was performed on the OSY-DF peptide using a 16.5%, 8- by 10-cm Tris-Tricine/peptide precast gel system (READY GEL®; Bio-Rad, Laboratories, Inc., Hercules, Calif.) (28, 32). After electrophoresis, one-half of the gel was stained with Coomassie blue G-250, while the other was washed three times, 15 min each, with sterile distilled water (Whitford, M. F., et al. (2001) *Appl. Environ. Microbiol.* 67:569-574.) and then overlaid with MRS soft agar seeded with *L. plantarum* ATCC 8014. The latter was examined for antimicrobial activity after overnight incubation at 30° C.

LC-MS. The antimicrobial CE fraction was analyzed by liquid chromatography-MS (LC-MS) under the same conditions as described for the HPLC purification, except that 15 μl of sample was injected. A Micromass LCT (Wythenshawe, United Kingdom) with an orthogonal electrospray source (Z-spray) was coupled to the outlet of the HPLC using a T-splitter. Samples were infused into the electrospray source at a flow rate of about 20 µl/min. For optimum electrospray ionization conditions, capillary voltage was 3 kV, source temperature was 100° C., and cone voltage was 50 V. Sodium iodide was used as an external mass calibration standard over the m/z range of 500 to 2,500. Data were acquired in continuum mode at the rate of 1 scan/s. All spectra were obtained in the positive ion mode.

Figure 2:
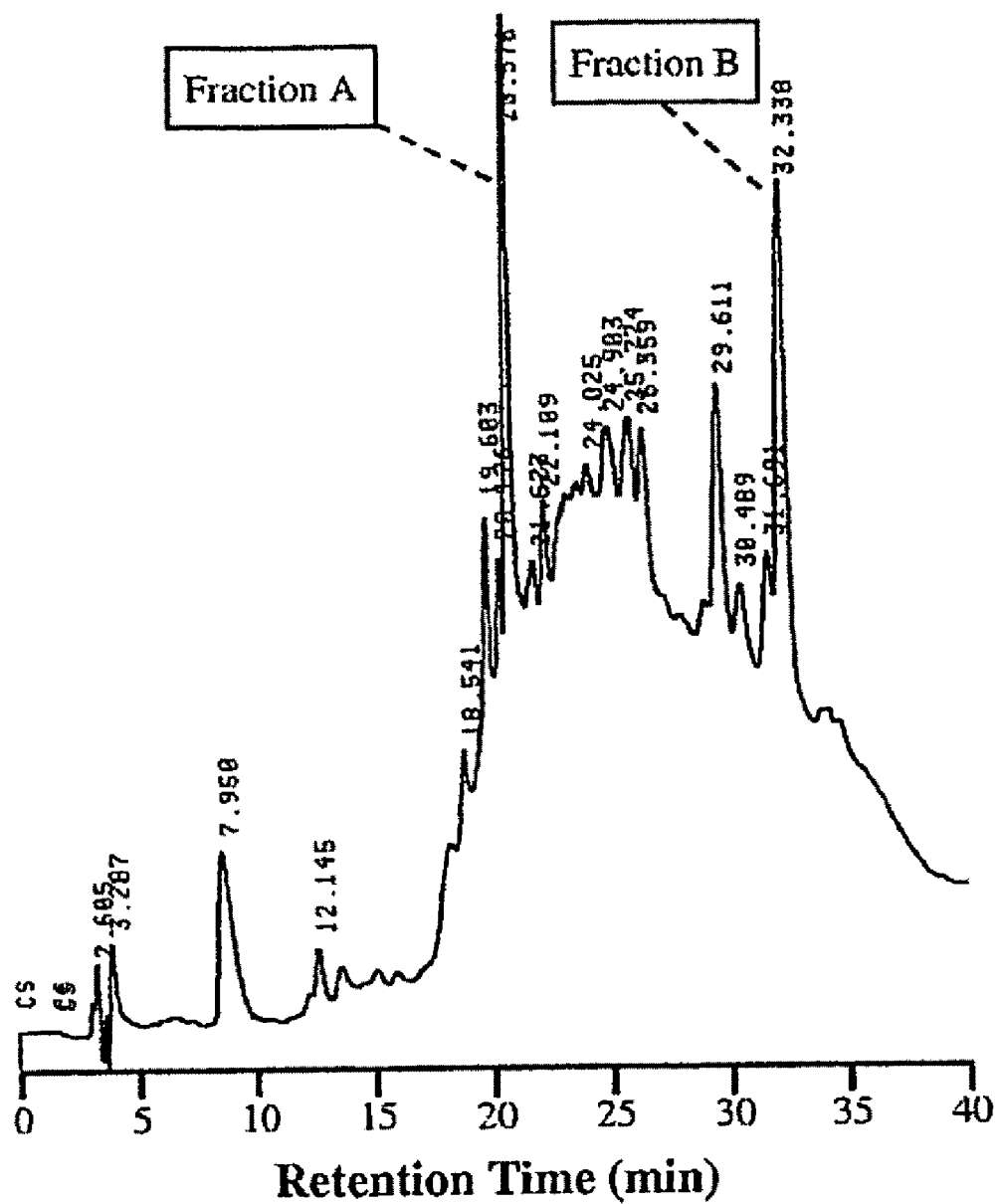
FIG. 2. High performance liquid chromatography profile of crude extract of *Paenibacillus polymyxa* OSY-DF culture supernatant. Fraction A, having activity against *Escherichia coli* K12; Fraction B, having activity against *Lactobacillus plantarum* ATCC 8014.
Figure 3:
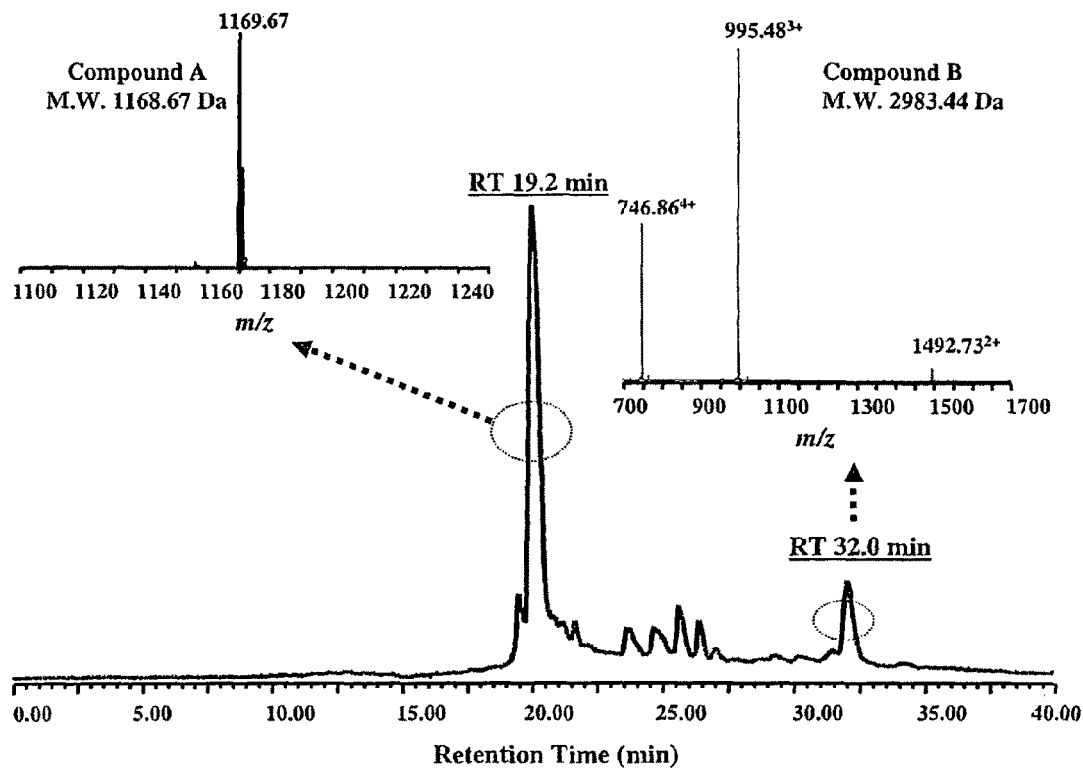
FIG. 3. Liquid chromatography-mass spectroscopy (LC-MS) profile of crude extract of *Paenibacillus polymyxa* OSY-DF culture supernatant.

RESULTS—Several commercially available microbiological media were tested for supporting the growth and production of antimicrobials by the OSY-DF strain. Among these media, TSBYE supported the highest antimicrobial potency (1,600 AU/ml) when the culture supernatant was tested against E. coli K-12 or L. plantarum ATCC 8014. Extraction of the antimicrobial substances from OSY-DF fermentate was achieved using Amberlite XAD-7 adsorbent, a nonionic macro-reticular resin that adsorbs and releases ionic species through hydrophobic and polar interactions. By applying XAD-7 resin to cell-free culture supernatant, the antimicrobial substances were selectively adsorbed, whereas most other water-soluble components remained in the liquid phase. The antimicrobial substances were eluted from XAD-7 by 75% ethanol, and the resulting fraction was freeze-dried to a CE powder, which retained most of the antimicrobial activity. Components of CE were separated further by HPLC, using a specialized column. In the HPLC profile, fractions corresponding to two peaks with retention times (RT) of 20 min and 32 min were active against E. coli K-12 and L. plantarum ATCC 8014, respectively (FIG. 2). These results suggest that OSY-DF produces dual antimicrobial compounds with different antimicrobial spectra. The chemical nature of OSY-DF antimicrobial compounds was elucidated by LC-MS (FIG. 3). This analysis produced a chromatographic profile similar to that observed earlier in the HPLC results, except for minor shifts in the RT, which may have been caused by the reduced loading volume (from 30 to 15 µl) and differences in system void volumes.

Data from LC-MS analysis showed that the fraction corresponding to a 19.2-min RT contains a pure compound (compound A) with a molecular mass of 1,168.67 Da. Association of this fraction with the anti-gram-negative activity of the OSY-DF cell extract was confirmed by the bioassay. Subsequent MS/MS analysis of compound A showed a fragmentation pattern identical to that of polymyxin E1 (see FIG. 9), an antibiotic that is specifically active against gram-negative bacteria.

Figure 4:
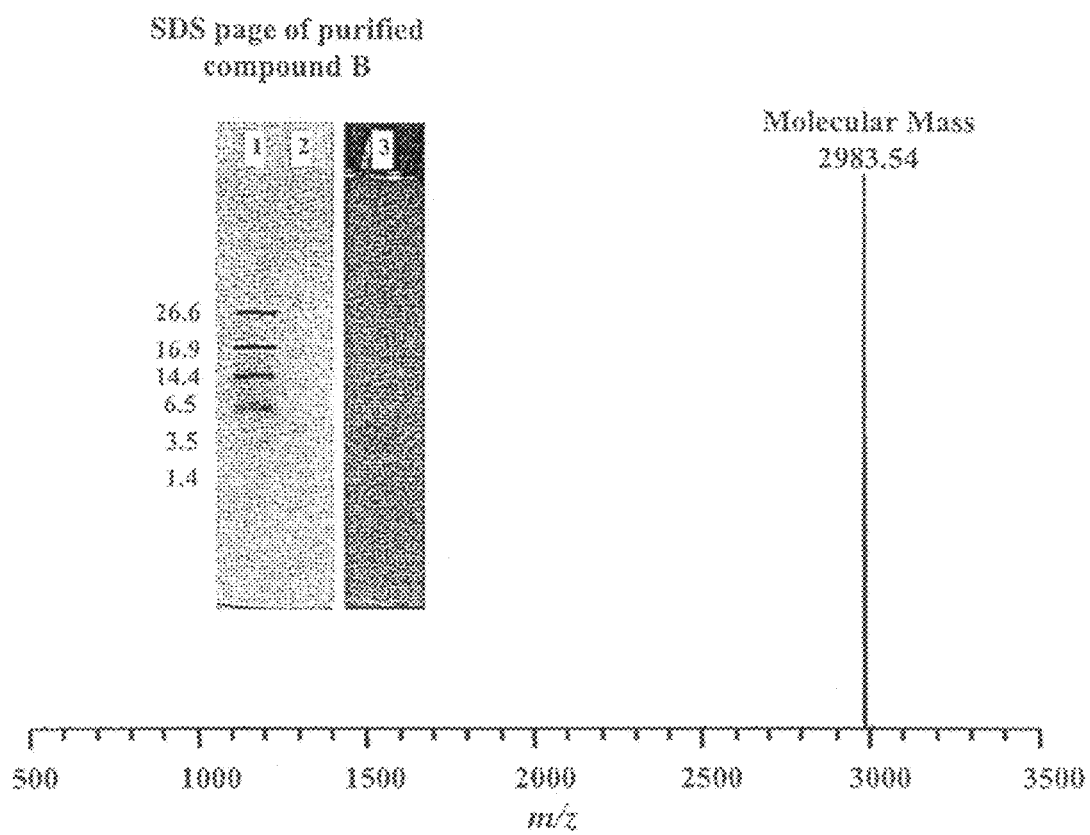
FIG. 4. Verification of the molecular mass and purity of compound B, as determined by MALDI-TOF-MS analysis (main figure) and SDS-PAGE (figure insert). Lanes 1 and 2: molecular mass marker (kDa) and purified paenibacillin, stained with Coomassie Blue G-250; lane 3: purified paenibacillin, overlaid with soft agar containing *Lactobacillus plantarum* ATCC 8014 after incubation.

Another compound in the 32.0-min RT fraction (compound B) had a molecular mass of 2,983.44 Da, and it was active against gram-positive bacteria. Compound B was further purified to homogeneity by using the established HPLC procedures, and it was analyzed by MALDITOF MS for purity and molecular mass verification. Results of this analysis (FIG. 4) proved this HPLC-purified agent contained only one compound with identical molecular mass to the one obtained earlier in the LC-MS experiment. When compound B was subjected to SDS-PAGE, only a single band (~3,000 Da) was detected (FIG. 4), confirming the high purity of the antimicrobial compound in the sample. The unstained half of the gel was overlaid with soft agar seeded with Lb. plantarum ATCC 8014; this produced an inhibition zone that corresponded to the band observed in the stained half (FIG. 4). This SDS-PAGE experiment and the subsequent analysis by proteolytic enzymes, as described later, confirmed the proteinaceous nature of compound B; this peptide was designated as paenibacillin.

Example 4

Antimicrobial Activity and Stability of Paenibacillin

RESULTS Purified paenibacillin was active against a panel of food-borne grampositive pathogenic and spoilage bacteria, including Bacillus spp., Clostridium sporogenes, Lactobacillus spp., Lactococcus lactis, Lactococcus mesenteroides, Listeria spp., Pediococcus cerevisiae, S. aureus, and Streptococcus agalactiae, but it was inactive against gram negatives (Table 1). Although paenibacillin targets gram-positive organisms only, it has a considerably broad antimicrobial spectrum within this group of bacteria.

The purified paenibacillin was also tested for sensitivity to changes in pH and temperature. Paenibacillin retained most of its antimicrobial activity, as judged by the results of the spot-on-lawn bioassay, when (i) held at 30, 37, 50, or 75° C. for 3 days, (ii) autoclaved at 121° C. for 5 min, or (iii) subjected to different pH values from 2.0 to 9.0 (data not shown). Purified paenibacillin lost its activity totally and partially when digested with ficin and trypsin, respectively (data not shown); this provides additional evidence for its proteinaceous nature. However, the antimicrobial activity of paenibacillin was not affected by β-amylase or lipase, implying that the compound is a pure peptide, without polysaccharide or lipid moieties.—

Sensitivity to heat, pH, and degradative enzymes. Crude extracts of Paenibacillus polymyxa OSY-DF and the HPLC-purified OSY-DF peptide were readily soluble in neutral water. The purified peptide was tested for sensitivity to heat, pH changes, and degradative enzymes. The qualitative spot-on-lawn bioassay was used to monitor the changes in antimicrobial potency after these treatments. For thermal stability testing, aliquots of OSY-DF peptide solution were exposed to 25, 30, 37, 50, and 70° C. for 72 h and 120° C. for 5 min. For the pH stability test, solutions of OSY-DF peptide were adjusted to pH 2.0, 3.0, 4.0, 5.0, 6.0, 7.0, 8.0, and 9.0, followed by incubation at 25° C. for 2 h. The residual antimicrobial activity was assessed after neutralizing the sample to pH 6.5.

Sensitivity of the OSY-DF peptide to various degradative enzymes was determined. Enzymes tested were α-chymotrypsin (48 U/mg), β-amylase (26.8 U/mg), bromelain (1.15 U/mg), ficin (0.22 U/mg), lipase (type I; 7.9 U/mg), papain (1.5 U/mg), protease (type XIII; 0.6 U/mg), and trypsin (10, 700 U/mg). All enzymes were purchased from Sigma, and their solutions were prepared in 25 mM phosphate buffer, pH 7.0, each containing 1 mg/ml except lipase solution, which contained 0.1 mg/ml. Solutions of the antimicrobial peptide were prepared in the same buffer. All stock solutions were separately sterilized by filtrating through low-protein binding filter (MILLEX-GV 0.22-_m filter unit; Millipore, Carrigtwohill, County Cork, Ireland). The stock solutions of OSY-DF peptide and enzymes were mixed at a 1:1 ratio (vol/vol) and incubated at 37° C. for 1 h before residual antimicrobial activity measurement.

Example 5

Amino Acid Sequencing of Native Paenibacillin

N-terminal amino acid sequence determination. The purified antimicrobial peptide was subjected to Edman degradation and analyzed by a protein sequencing system (model 494, Procise sequencing system; Applied Biosystems) at the Microchemistry and Proteomics Analysis Facility, Harvard University (Cambridge, Mass.) using standard protocols (Cornwell, G. G., et al. (1988) Biochem. Biophys. Res. Commun. 154:648-653; Wescombe, P. A. and J. R. Tagg. (2003) Appl. Environ. Microbiol. 69:2737-2747.).

MALDI-TOF analysis. The purified peptide was subjected to matrix-assisted laser desorption ionization-time of flight mass spectrometry (MALDI-TOF MS) analysis. The matrix, α-cyano-4-hydroxy cinnamic acid, was prepared as a saturated solution in 50% acetonitrile with 0.1% TFA in water. Aliquots consisting of 5 µl matrix and 1 µl sample were thoroughly mixed, spotted (1.0 µl) on the target plate, and allowed to air dry. Analysis was performed on a Bruker Reflex III time-of-flight mass spectrometer (Bruker Daltonics Inc., Billerica, Mass.) operated in reflection positive ion mode at an accelerating voltage of 28 kV. The $N_2$ laser was operated at the minimum threshold level required to generate signal and minimize dissociation.

Quadrupole-time of flight MS/MS. The native OSY-DF peptide was further investigated on a Micromass Q-Tof™ II apparatus (Micromass, Wythenshawe, United Kingdom) equipped with an orthogonal electrospray source (Z-spray) and operated in positive ion mode. For external mass calibration, NaI was used over the m/z range of 200 to 2,500. The antimicrobial peptide, dissolved in the mixture of $H_2O$: $CH_3OH$:HAc (50:50:2.5), was infused into the electrospray source at a 2 µl/min flow rate. To achieve the optimal electrospray, capillary voltage was set at 3,000 V, source temperature was 150° C., and cone voltage was 60 V. The first quadrupole, Q1, was set to pass ions between 200 and 2,500 m/z. The target ion was isolated and fragmented within the second quadrupole by adding a voltage of between 20 and 40 V. The fragment ions were then analyzed in the time-of-flight tube. Data were acquired in continuum mode until well-averaged data were obtained.

NMR analysis. Purified and lyophilized OSY-DF peptide (~43 mg) was dissolved into 600 ml 99.9% deuterium oxide (D2O; Cambridge Isotope Lab., Andover, Mass.). One-dimensional $^1$H-NMR spectroscopy and two-dimensional $^1$H-homonuclear total correlation spectroscopy (TOCSY) were performed at 20° C. on a Bruker DMX-600 spectrometer (Bruker BioSpin GmbH, Rheinstetten, Germany) equipped with a triple resonance probe as well as three-axis gradient coils. The two-dimensional TOCSY experiment employed a DIPSI2 mixing sequence with the sensitivity enhancement feature (Cavanagh, J., and M. Rance. (1990) *J. Magn. Reson.* 88:72-85). The spectral width and mixing time were 6,600 Hz and 60 ms, respectively. The data were recorded with 2,048 time-domain complex points, 210 increments in the indirectly detected dimension, and 96 scans per t1 increment. Data were processed using XWINNMR 3.1 software (Bruker). Briefly, the appropriate window function was applied on each dimension followed by Fourier transformation and baseline correction. Chemical shifts were referenced to the external standard, 2,2-dimethyl-2-silapentane-5-sulfonate.

Figure 5:
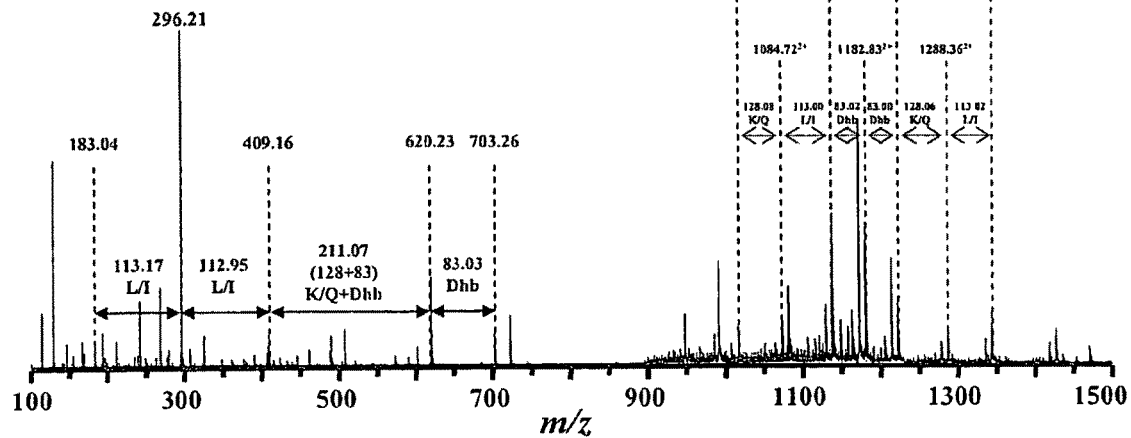
FIG. 5. Mass spectroscopy/Mass spectroscopy (MS/MS) sequencing of native paenibacillin. Partial sequence was identified as -Leu/Ile-Leu/Ile-Lys/Gln-Dhb-Dhb-Leu/Ile-Lys/Gln-. Leu/Ile and Lys/Gln cannot be differentiated due to the identical and similar molecular masses, respectively.
Figure 6:
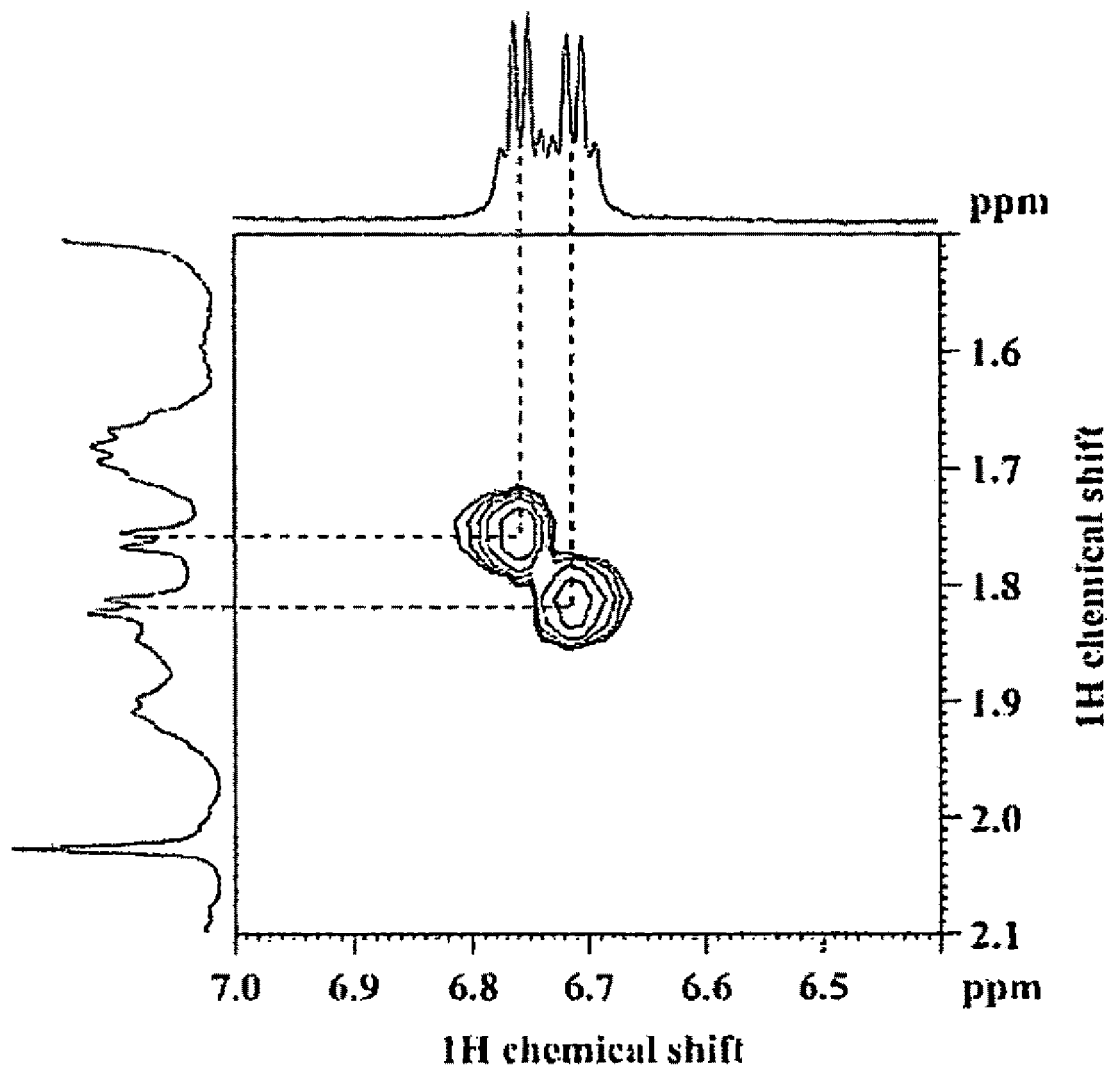
FIG. 6 NMR evidence for the existence of two Dhb residues in paenibacillin. The expansions of NMR spectra showing the unique quartet peaks of $H^\beta$ at ~6.7 ppm in 1D $^1$H NMR (top) and the through-bond cross peaks between $H^\beta$ and $H^\gamma$ (~1.80 ppm) in the TOCSY experiment (middle).

RESULTS_No amino acid residues were detected by direct N-terminal amino acid sequencing (Edman degradation) of paenibacillin. Consequently, it was hypothesized that the N terminal of the peptide is blocked by an unusual structure. Sequencing the native peptide using MS/MS analysis was only partially successful. As shown in FIG. 5, little cleavage was observed between 720 and 1,200 (m/z), suggesting the presence of an intramolecular thioether bridge (Lan and/or MeLan), a common feature among lantibiotics; such a bridge may have impeded the fragmentation of native paenibacillin during the MS/MS analysis. Nevertheless, a partial sequence was revealed: Leu/Ile-Leu/Ile-Lys/Gln-Dhb-Dhb-Leu/Ile-Lys/Gln or, in the reverse order, Lys/Gln-Leu/Ile-Dhb-Dhb-Lys/Gln-Leu/Ile-Leu/Ile, in which Leu and Lys could not be differentiated from Ile and Gln, respectively, due to the same (Leu/Ile) or virtually identical (Lys/Gln) masses (FIG. 5). Analysis by NMR also confirmed the presence of Dhb residues (FIG. 6), which were readily identified by the unique quartet peaks of $H^\beta$ at ~6.7 ppm in the 1D $^1$H NMR spectroscopy and the through-bond crosspeaks between $H^\beta$ and $H^\gamma$ (~1.80 ppm) in the TOCSY experiment (van de Kamp, M., et al. (1995) *Eur. Biochem.* 230:587-600; van de Kamp, M., et al. (1995) *Eur. J. Biochem.* 227:757-771). Although limited information was obtained on the native paenibacillin, the observation of a fragment containing Dhb tandem, together with crude information regarding the several flanking residues, is sufficiently unique to claim that the peptide is a novel lantibiotic. This conclusion is further strengthened in the following work on the chemically modified peptide.

Example—6

Elucidating the Paenibacillin Sequence after Chemical Modification and Enzyme Digestion $Ni_2B$-based desulfurization/reduction of the antimicrobial peptide. The peptide modification reaction was adapted from the methods of Martin et al. (2004), *Biochemistry* 43:3049-3056. A portion (~0.5 mg) of the OSY-DF peptide was dissolved in a 70:30 (vol/vol) methanol-water solution containing 0.1% TFA. Ten mg NiCl2 (Sigma) was added to 1 ml peptide solution, and the suspension was stirred until the solution became clear. The resulting solution was transferred to a 1.5-ml screw-cap flask containing 10 mg NaBH4 (Sigma) and sealed rapidly. A black precipitate formed immediately (Ni2B), with evolution of hydrogen gas. The mixture was then stirred for 1 h at 50° C. followed by centrifugation to separate Ni2B precipitate from the supernatant. The Ni2B precipitate was washed sequentially by (i) 0.5 ml methanol, (ii) water, and (iii) 70:30 methanol-water (all solvents contained 0.1% TFA). Each washing was followed by centrifugation and decanting the wash solution. All the decanted wash solutions were analyzed as described below.

Tryptic digestion profile of modified antimicrobial peptide. Sequencing-grade trypsin (Promega) was added to the modified OSY-DF peptide in 100 mM $NH_4HCO_3$ buffer (pH 8.0). The mixture, with a 1:25 enzyme-substrate ratio (wt/wt), was incubated at 37° C. for 16 h before quenching by adding 0.1% TFA. Samples were then desalted with a peptide desalting trap (Michrom BioResources Inc., Auburn, Calif.) before mass spectrometric analysis.

MALDI-TOF analysis. The chemically-modified OSY-DF peptide was subjected to matrix-assisted laser desorption ionization-time of flight mass spectrometry (MALDI-TOF MS) analysis, by using the same methods as described in example 4.

Quadrupole-time of flight MS/MS. The chemically-modified OSY-DF peptide was further investigated on a Micromass Q-Tof™ II apparatus (Micromass, Wythenshawe, United Kingdom) equipped with an orthogonal electrospray source (Z-spray) and operated in positive ion mode, by using the same methods as described in example 4.

Figure 7:
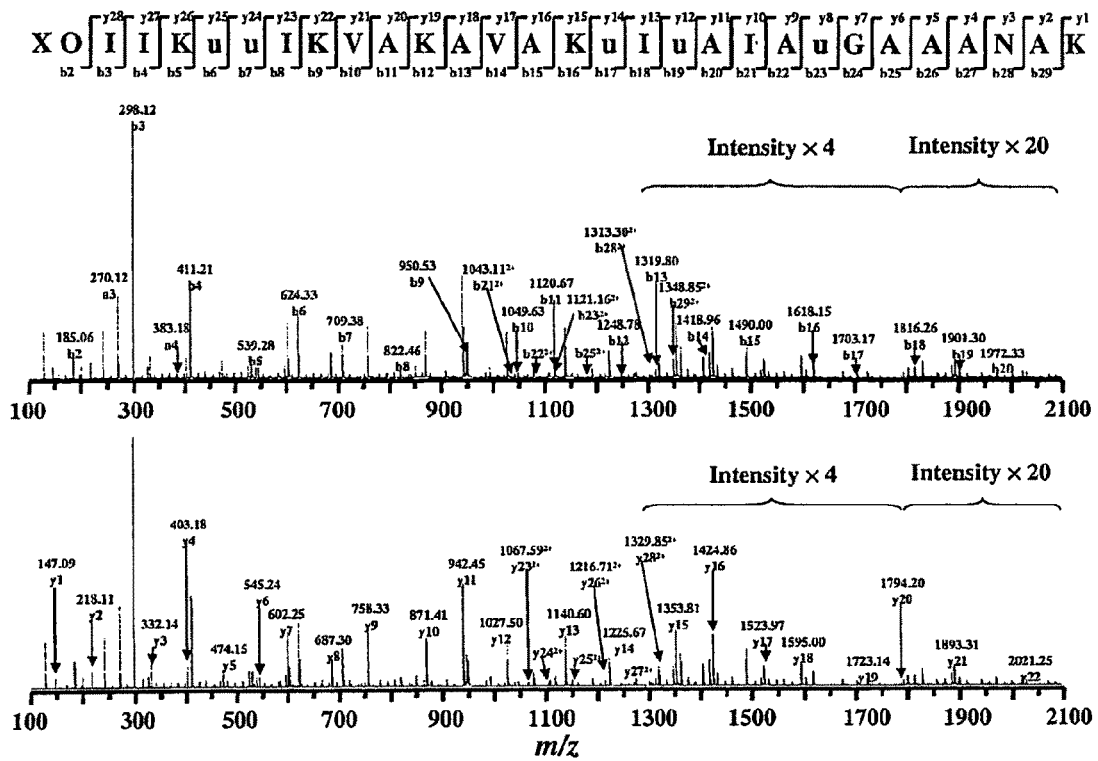
FIG. 7. MS/MS sequencing results of the modified paenibacillin (SEQ ID NO: 9); Lys 5, 9, 12, 16 and 30 cannot be differentiated from Gln due to the similar mass, whereas Ile in 3, 4, 8, 18 and 21 cannot be distinguished from Leu due to the identical mass.

RESULTS—The newly reported $Ni_2B$ based desulfurization/reduction approach, which converts an intralinked lantibiotic into a linear structure, significantly facilitated the sequencing of paenibacillin by MS/MS analysis. In such a treatment, a Lan is converted into two Ala and MeLan is converted into Ala and Abu, while Dha and Dhb are reduced to Ala and Abu, respectively. The method has been adapted and successfully applied to paenibacillin, and the following sequential information was obtained for this chemically modified form: X-O-Leu/Ile-Leu/Ile-Lys/Gln-Abu-Abu-Leu/Ile-Lys/Gln-Val-Ala-Lys/Gln-Ala-Val-Ala-Lys/Gln-Abu-Leu/Ieu-Abu-Ala-Leu/Ile-Ala-Abu-Gly-Ala-Ala-Ala-Asn-Ala-Lys/Gln (SEQ ID NO: 6), in which X and O are yet undetermined and ambiguities still remained regarding the Leu/Ile and Lys/Gln identification (FIG. 7; Table 2).

TABLE 2

Detailed MS/MS analysis of paenibacillin reduced with NaBH4 and NaBD4

| Δm between y-n (D) and y-n (H) | Fragment Ion | Measured m/z (NaBD4) | Measured m/z (NaBH4) | Sequence (SEQ ID NO: 7) | Measured m/z (NaBD4) | Measured m/z (NaBH4) | Fragment Ion | Δm between b-n (D) and b-n (H) |
|---|---|---|---|---|---|---|---|---|
| | | | | X | | | | |
| | | | | O (2) | 187.02 | 185.06 | b-2 | 1.96 |
| | y-28 | | 1329.85$^{2+}$ | Leu | 300.13 | 298.12 | b-3 | 2.01 |
| 16.02 | y-27 | 1281.29$^{2+}$ | 1273.28$^{2+}$ | Leu | 413.21 | 411.21 | b-4 | 2.00 |
| 16.06 | y-26 | 1224.74$^{2+}$ | 1216.71$^{2+}$ | Lys | 541.27 | 539.28 | b-5 | 1.99 |
| 15.98 | y-25 | 1160.65$^{2+}$ | 1152.66$^{2+}$ | Abu(2) | 628.33 | 624.33 | b-6 | 4.00 |
| 14.00 | y-24 | 1117.12$^{2+}$ | 1110.12$^{2+}$ | Abu(2) | 715.41 | 709.38 | b-7 | 6.03 |
| 12.06 | y-23 | 1073.62$^{2+}$ | 1067.59$^{2+}$ | Leu | 828.48 | 822.46 | b-8 | 6.02 |
| 12.01 | y-22 | 1017.13$^{2+}$ | 2021.25 | Lys | 956.53 | 950.53 | b-9 | 6.00 |
| | y-21 | | 1893.31 | Val | 1055.61 | 1049.63 | b-10 | 5.98 |
| 11.98 | y-20 | 903.59$^{2+}$ | 1794.20 | Ala(1) | 1127.69 | 1120.67 | b-11 | 7.02 |
| 11.00 | y-19 | 867.57$^{2+}$ | 1723.14 | Lys | 1255.77 | 1248.78 | b-12 | 6.99 |
| 10.98 | y-18 | 803.49$^{2+}$ | 1595.00 | Ala(0) | 663.89$^{2+}$ | 1319.80 | b-13 | 6.98 |
| 10.96 | y-17 | 1534.93 | 1523.97 | Val | 713.46$^{2+}$ | 1418.96 | b-14 | 6.96 |
| 11.02 | y-16 | 1435.88 | 1424.86 | Ala(1) | 749.49$^{2+}$ | 1490.00 | b-15 | 7.98 |
| 10.95 | y-15 | 682.38$^{2+}$ | 1353.81 | Lys | 813.56$^{2+}$ | 1618.15 | b-16 | 7.97 |
| 10.01 | y-14 | 1235.68 | 1225.67 | Abu(1) | 856.57$^{2+}$ | 1703.17 | b-17 | 8.97 |
| 9.01 | y-13 | 1149.61 | 1140.60 | Leu | 913.16$^{2+}$ | 1816.26 | b-18 | 9.06 |
| 9.01 | y-12 | 1036.52 | 1027.50 | Abu(1) | | 1901.30 | b-19 | |
| 8.01 | y-11 | 950.46 | 942.45 | Ala(1) | 992.14$^{2+}$ | 1972.33 | b-20 | 10.95 |
| 7.01 | y-10 | 878.42 | 871.41 | Leu | 1048.59$^{2+}$ | 1043.11$^{2+}$ | b-21 | 10.96 |
| 7.01 | y-9 | 765.34 | 758.33 | Ala(1) | | 1078.64$^{2+}$ | b-22 | |
| 6.00 | y-8 | 693.30 | 687.30 | Abu(1) | 1127.69$^{2+}$ | 1121.16$^{2+}$ | b-23 | 13.06 |
| 5.02 | y-7 | 607.27 | 602.25 | Gly | | 1149.68$^{2+}$ | b-24 | |
| 5.01 | y-6 | 550.25 | 545.24 | Ala(1) | 1192.20$^{2+}$ | 1185.21$^{2+}$ | b-25 | 13.98 |
| 4.00 | y-5 | 478.21 | 474.21 | Ala(1) | | 1220.74$^{2+}$ | b-26 | |
| 3.00 | y-4 | 406.18 | 403.18 | Ala(2) | 1264.80$^{2+}$ | 1256.27$^{2+}$ | b-27 | 17.06 |
| 0.99 | y-3 | 333.13 | 332.14 | Asn | 1321.78$^{2+}$ | 1313.30$^{2+}$ | b-28 | 16.96 |
| 1.00 | y-2 | 219.11 | 218.11 | Ala(1) | | 1348.85$^{2+}$ | b-29 | |
| −0.01 | y-1 | 147.08 | 147.09 | Lys | | | | |

* (1)/(2) in the sequence column represents the mass shift caused by deuterium labeling on that specific residue. A mass shift of 1 Da suggested this residue was from Lan or MeLan while a mass shift of 2 Da suggested this residue is from Dha or Dhb.

Figure 8:
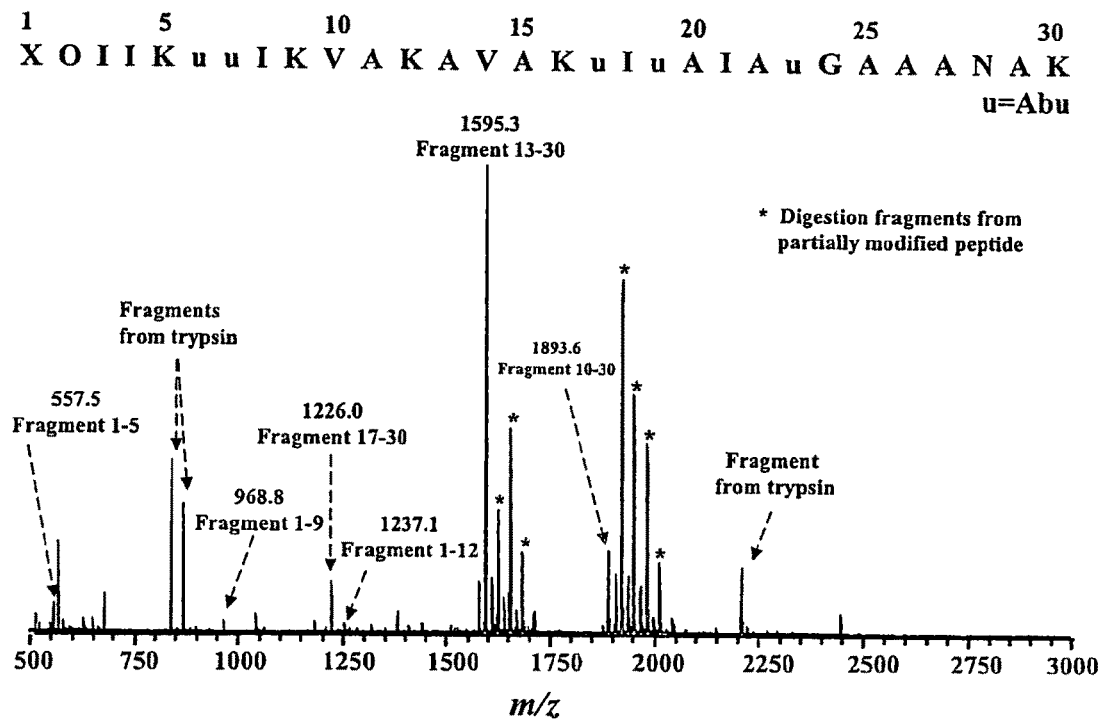
FIG. 8. MALDI-TOF MS analysis of tryptic digestion product of modified paenibacillin (SEQ ID NO: 9), confirming the presence of Lys5, 9, 12 and 16, whereas Lys/Gln30 remains undetermined; Leu and Ile also remain undistinguishable.

After digestion of modified paenibacillin with trypsin, which specifically cleaves at Arg and Lys but not Gln, all Lys residues but one at the C terminus were determined (FIG. 8). The desulfurization/reduction reaction was repeated with a deuterated reducing agent, sodium borodeuteride (NaBD4), followed by MS/MS analysis. Since two deuterium atoms were added to the double bonds in both Dha and Dhb, whereas only one deuterium atom was added to either Abu in MeLan or Ala in Lan, the mass shift of the isotope effect provides a means to differentiate the sources of Ala and Abu in the variant peptide (Martin et al., (2004) *Biochemistry* 43:3049-3056). The results of this analysis are summarized in Table 2. For example, a 2-Da mass shift was observed on Abu6, Abu7, and Ala27, leading to the confirmation and identification of Dhb6, Dhb7, and Dha27 in the native form. On the other hand, only a 1-Da mass shift was observed in Abu17, Abu19, Abu23, Ala11, Ala15, Ala20, Ala22, Ala25, Ala26, and Ala29, inferring the existence of three MeLan and two Lan thioether bridges. Lastly, the Edman degradation method was repeated on this chemically modified paenibacillin, but no amino acid residues were detected during this sequencing attempt. This result implies that the N terminus of paenibacillin is blocked for an unknown reason. However, the 2-Da mass shift, observed for the X—O fragment (183.05 Da in the native form versus 185.05 Da in the reduced form), suggests the presence of Dha, Dhb, or a variant of these residues in the N-terminal XO region (Table 2). Taken together, a tentative sequence with 15 modified residues (in italics) is proposed for the native paenibacillin: (X-Dha/Dhb)-Leu/Ile-Leu/Ile-Lys-Dhb-Dhb-Leu/Ile-Lys-Val-Ala-Lys-Ala-Val-Ala-Lys-Abu-Leu/Ile-Abu-Ala-Leu/Ile-Ala-Abu-Gly-Ala-Ala-Dha-Asn-Ala-Lys/Gln (SEQ ID NO: 8), where the highlighted Abu and Ala residues are engaged in the formation of Lan or MeLan thiother bridges.

Example 7

Sequencing of Paenibacillin by Extensive NMR

Lantibiotics are group I bacteriocins that are synthesized and post-translationally modified by Gram-positive bacteria. These modifications generate dehydrated amino acids, i.e., α,β-didehydroalanine (Dha) and α,β-didehydrobutyric acid (Dhb) and thioether bridges of lanthionine (Lan) and β-methyllanthionine (MeLan), as well as some other less frequently encountered modifications. (FIG. 10). These modified residues are believed to stabilize molecular conformations that are essential for the antimicrobial activity of lantibiotics and their resistance to proteases of the producing strains.

Paenibacillin was purified and studied by nuclear magnetic resonance spectroscopy in an effort to fully elucidate its primary structure. Extensive 2D homonuclear and heteronuclear NMR experiments, taken together with previous MS/MS results, led to the determination of the sequence of paenibacillin as (CH$_3$CO-A)-Dha-I-I-K-Dhb-Dhb-I-K-V-A(1)-K-A-V-A(1)-K-Abu(2)-L-Abu(3)-A(2)-I-A(3)-Abu(4)-G-A(5)-A(4)-Dha-N-A(5)-K (SEQ ID NO: 5), where A and Abu are alanine and β-methylalanine moieties, respectively; and the numbers in parentheses indicate their pairings in the formation of Lan (A-S-A) or MeLan (Abu-S-A) thioether bridge. It is concluded that (i) paenibacillin is a type-A lantibiotic, with a linear structure and a net positive charge at neutral pH; (ii) The peptide, with unusual residues (italicized) accounting for half of the sequence, is one of the most post-translationally modified lantibiotics; (iii) The molecule is having a distinctly constrained C-terminus due to the presence of five thioether bridges, four of which are intertwined; and (iv) most surprisingly, this lantibiotic has an acetylated N-terminal, which—to the best of our knowledge—is unprecedented among bacteria-derived antimicrobial peptides. In conclusion, paenibacillin is a unique type-A lantibiotic with a relatively large number of modified residues and intertwined thioether bridges. This peptide also is distinguishable from other type-A lantibiotics by its salient feature of N-terminal acetylation, a common event in intracellular eukaryotic proteins but rare in prokaryotic organisms. Considering the exogenous maturation nature of lantibiotic, these findings suggest that N-terminal acetylation occurs in bacteria-derived lantibiotics by a unique post-translational and extracellular manner.

Enhanced Production and Purification of Paenibacillin

Paenibacillin was produced in *Paenibacillus polymyxa* OSY-DF cultures and the peptide was purified as described above with modifications. Measures taken to enhance the yield of paenibacillin include (i) flasks with extra-deep baffle were used to increase oxygen transfer during fermentation, leading to an improved antimicrobial titer, (ii) a preparative HPLC C-18 reverse-phase column (Alltima, 250×10-mm, 5 µm; Alltech, Deerfield, Ill., USA) was used to allow the purification of relatively large quantity of sample, and (iii) the HPLC conditions were modified: linear biphasic gradient of 20-40% methanol in 0.1% TFA aqueous solution was applied over 15 min, then 40-60% over 10 min, and finally 60-70% over 20 min, at a flow rate of 3.0 ml/min. Paenibacillin-rich fractions were pooled and examined by SDS-PAGE and mass spectroscopy for purity (see above). High purity paenibacillin powder (white) was obtained after lyophilization and stored at −20° C. before further testing. A reference compound (N-Acetyl-L-alanine) for the NMR analysis of N-terminal capping (Sigma-Aldrich, St. Louis, Mo.) was used without further purification.

Detection of Native Paenibacillin in Fermentation Broth

To detect paenibacillin in its native form, aliquots (5 ml) of fermentate were withdrawn aseptically at 0, 12 and 24 h of fermentation. After centrifugation, the resulting cell-free supernatants were collected and analyzed by matrix-assisted laser-desorption/ionization time-of-flight mass spectroscopy (MALDI-TOF MS) on a Bruker Reflex III (Bruker Daltonics Inc, Billerica, Mass.), as described above.

NMR Experiments

A portion (~1 mg) of the highly-purified lyophilized paenibacillin was dissolved in 99.996% $D_2O$ (Cambridge Isotope Lab., Andover, Mass.), and another portion (4.3 mg) was dissolved into 90% $H_2O$/10% $D_2O$ (referred to as $H_2O$, thereafter), both at pH 4.5. Solvent signal suppression in NMR experiments was typically achieved by pre-saturation during the relaxation delay for the sample dissolved in $D_2O$ and 3-9-19 WATERGATE (Sklenar, V., et al. (1993) *J Magn Reson A* 102, 241-245) prior to detection for the sample dissolved in $H_2O$ with the proton transmitter offset placed on the water resonance. All but one experiment were performed on a Bruker DMX-600 spectrometer equipped with a triple-resonance probe and three-axis gradient coils. The following experiments, running at 293.9 K with Bruker standard pulse sequences, were carried out:

A. 2D $^1H$-homonuclear experiments: DQF-COSY (Rance, M., et al. (1983) *Biochem. Biophys. Res. Commun.* 117(2), 479-485), TOCSY (Cavanagh, J., and Rance, M. (1990) *J. Mag. Reson.* 88(1), 72-85) with 60 ms DIPSI-2 (Shaka, A. J., et al. (1988) *J. Mag. Reson.* 77(2), 274-293) mixing time, NOESY (Jeener, J., et al. (1979) *J. Chem. Phys.* 71(11), 4546-4553) with 200, 450, and 700 ms mixing times, and ROESY (Bothner-By, A. A., et al. (1984) *J. Am. Chem. Soc.* 106(3), 811-813) with 200 ms mixing time.

B. 2D $^1H$-$^{13}C$ heteronuclear experiments: HSQC (Kay, L. E., et al. (1992) *J. Am. Chem. Soc.* 114(26), 10663-10665), HMBC (Bax, A., and Summers, M. F. (1986) *J. Am. Chem. Soc.* 108(8), 2093-2094), HSQC-TOCSY, HSQC-NOESY and HSQC-ROESY at natural $^{13}C$ abundance.

C. 2D $^1H$-$^{15}N$ fast HSQC at natural $^{15}N$ abundance (Mori, S. A., C., et al. (1995) *J magn Reson B* 108, 94-98).

Some experiments were repeated at different temperatures (287.3 K and 301.8 K) to resolve ambiguities due to resonance overlapping. 2D $^1H$-$^{13}C$ HMBC was recorded twice, one with the sample dissolved in $D_2O$ on the Bruker DMX-600 spectrometer focusing on the $^1H^\alpha$-$^{13}C'$ region, and the other with the sample dissolved in $H_2O$ on a Bruker DRX-800 spectrometer (equipped with cryoprobe and z-axis gradient coil) revealing correlations. A typical data set is 2048* (f1)× 400* (f2), 96 scans per t1/t2 increment for a homonuclear experiment, and 1024* (f1)×128* (f2), 512 scans per t1/t2 increment for a heteronuclear experiment, where the asterisk denotes complex points, and f1 and f2 are the direct and indirect detected dimension, respectively. Relaxation delay is typically 1.5 s. The experiments are summarized in Table 3, including some of the important parameters used. Data were processed with XWINNMR 3.5 (Bruker BioSpin GmbH, Rheinstetten, Germany). Generally, one-time zero-filling was employed in the indirectly detected dimension, whereas Lorentzian-Gaussian or shifted sine bell window functions were applied on both dimensions followed by Fourier transformation and baseline correction. Both $^1H$ and $^{13}C$ chemical shifts were referenced to an external standard 2,2-dimethyl-2-silapentane-5-sulfonate (DSS), while $^{15}N$ was indirectly referenced via Ξ ratio (Wishart, D. S., et al. (1995) *J Biomol NMR* 6(2), 135-140). The chemical shift assignments were deposited in BioMagResoBank (http://www.bmrb.wisc.edu) under Accession No. 15489.

TABLE 3

Summary of 2D NMR experiments performed on paenibacillin*

| Experiments (number) | Solvent & TE | Mixing time (ms) | Matrix F2 (FID) × F1 (complex points) | Spectral width F2 × F1 (Hz) | NS/FID |
|---|---|---|---|---|---|
| Homonuclear | | | | | |
| DQF-COSY | $D_2O$, 293.9K | | 2048 × 400 | 6613 × 6601 | 64 |
| TOCSY | $D_2O$, 293.9K | 60 | 2048 × 420 | 6613 × 6601 | 96 |
| NOESY (2) | $D_2O$, 293.9K | 200, 450 | 2048 × 400 | 6613 × 6601 | 64 |
| NOESY | $D_2O$, 287.3K | 450 | 2048 × 400 | 6613 × 6601 | 96 |
| ROESY | $D_2O$, 293.9K | 200 | 1024 × 400 | 6613 × 6601 | 80 |

TABLE 3-continued

Summary of 2D NMR experiments performed on paenibacillin*

| Experiments (number) | Solvent & TE | Mixing time (ms) | Matrix F2 (FID) × F1 (complex points) | Spectral width F2 × F1 (Hz) | NS/FID |
|---|---|---|---|---|---|
| DQF-COSY | $H_2O$, 293.9K | | 2048 × 420 | 6613 × 6601 | 64 |
| TOCSY | $H_2O$, 293.9K | 60 | 2048 × 420 | 6613 × 6601 | 96 |
| TOCSY | $H_2O$, 301.8K | 60 | 2048 × 420 | 6613 × 6601 | 96 |
| TOCSY | $H_2O$, 287.3K | 60 | 2048 × 420 | 6613 × 6601 | 96 |
| NOESY (3) | $H_2O$, 293.9K | 200, 450, 700 | 2048 × 420 | 6613 × 6601 | 128 |
| NOESY | $H_2O$, 287.3K | 200 | 2048 × 420 | 6613 × 6601 | 128 |
| NOESY | $H_2O$, 301.8 | 200 | 2048 × 420 | 6613 × 6601 | 128 |
| Heteronuclear | | | | | |
| $^1H$-$^{13}C$ HSQC | $D_2O$, 293.9K | | 2048 × 256 | 7788 × 24146 | 128 |
| $^1H$-$^{13}C$ HSQC | $D_2O$, 293.9K | | 2048 × 512 | 6613 × 4527 | 128 |
| $^1H$-$^{13}C$ HSQC-NOESY | $D_2O$, 293.9K | 200 | 2048 × 256 | 7788 × 10564 | 128 |
| $^1H$-$^{13}C$ HSQC-TOCSY | $D_2O$, 293.9K | 60 | 2048 × 256 | 7788 × 10564 | 128 |
| $^1H$-$^{13}C$ HSQC-ROESY | $D2O$, 293.9K | 200 | 2048 × 256 | 7788 × 10564 | 128 |
| $^1H$-$^{13}C$ HMBC | $D_2O$, 293.9K | | 2048 × 256 | 6613 × 36223 | 128 |
| $^1H$-$^{13}C$ HMBC | $H_2O$, 293.9K | | 2048 × 64 | 9615 × 5030 | 512 |
| $^1H$-$^{15}N$ HSQC | $H_2O$, 287.3K | | 1024 × 128 | 7788 × 1763 | 512 |
| $^1H$-$^{15}N$ HSQC | $H_2O$, 293.9K | | 1024 × 128 | 7788 × 1763 | 512 |
| $^1H$-$^{15}N$ HSQC | $H_2O$, 301.8K | | 1024 × 128 | 7788 × 1763 | 512 |

*(a) All the TOCSY experiments used DIPSI2 for spin lock applied in $^1H$ dimension; (b) TE: temperature. (c) NS/FID: number of scans per t1/t2 increment. (d) F2 is directly detected dimension, whereas F1 is indirectly detected dimension. (e) States-TPPI is used in COSY, TOCSY and NOESY, Echo-Antiecho in HSQC experiments, and QF in HMBC.

Results

Detection of Paenibacillin in Fermentation Broth by MALDI-MS

Figure 11:
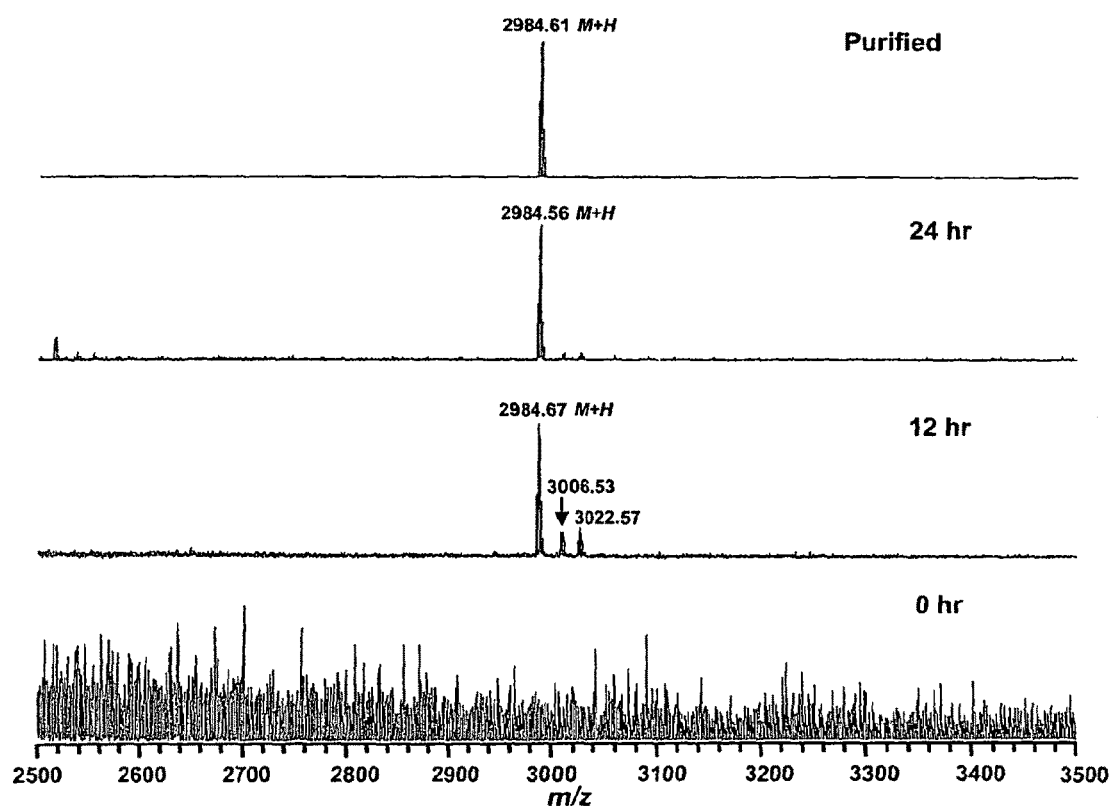
FIG. 11. Detection of native paenibacillin by MALDI-TOF MS spectra in *Paenibacillus polymyxa* OSY-DF fermentate taken at 0, 12 and 24 hr of fermentation. A mass identical to the HPLC-purified paenibacillin was detected at 12 and 24 h, suggesting that paenibacillin is the direct metabolite of *P. polymyxa* OSY-DF.

Paenibacillin was isolated from fermentation broth by XAD7-adsorption/desorption and the crude extract was then purified to homogeneity by applying reverse phase HPLC (see above). Since lantibiotics may degrade during preparation (van de Kamp, M., et al. (1995) *Eur J Biochem* 227(3), 757-771; Chan, W. C., et al. (1989) *FEBS Lett.* 252(1), 29-36), a control experiment was performed to detect the peptide in its native state, and confirm that the peptide remained intact after the chemical isolation and purification process. Briefly, the fermentation broth was sampled during the 24 hours of incubation followed by direct MALDI-MS analysis. As shown in FIG. 11. Samples collected at 12 and 24 h (but not at 0 h) yielded a signal that has an identical mass (2983.56 Da) to the HPLC-purified peptide (2983.53 Da). The result confirms that the sample, used in MS/MS and NMR investigation, is indeed the native form found in the fresh fermentate of *P. polymyxa* OSY-DF.

Preliminary Analysis by 1D $^1H$ NMR

Figure 12:
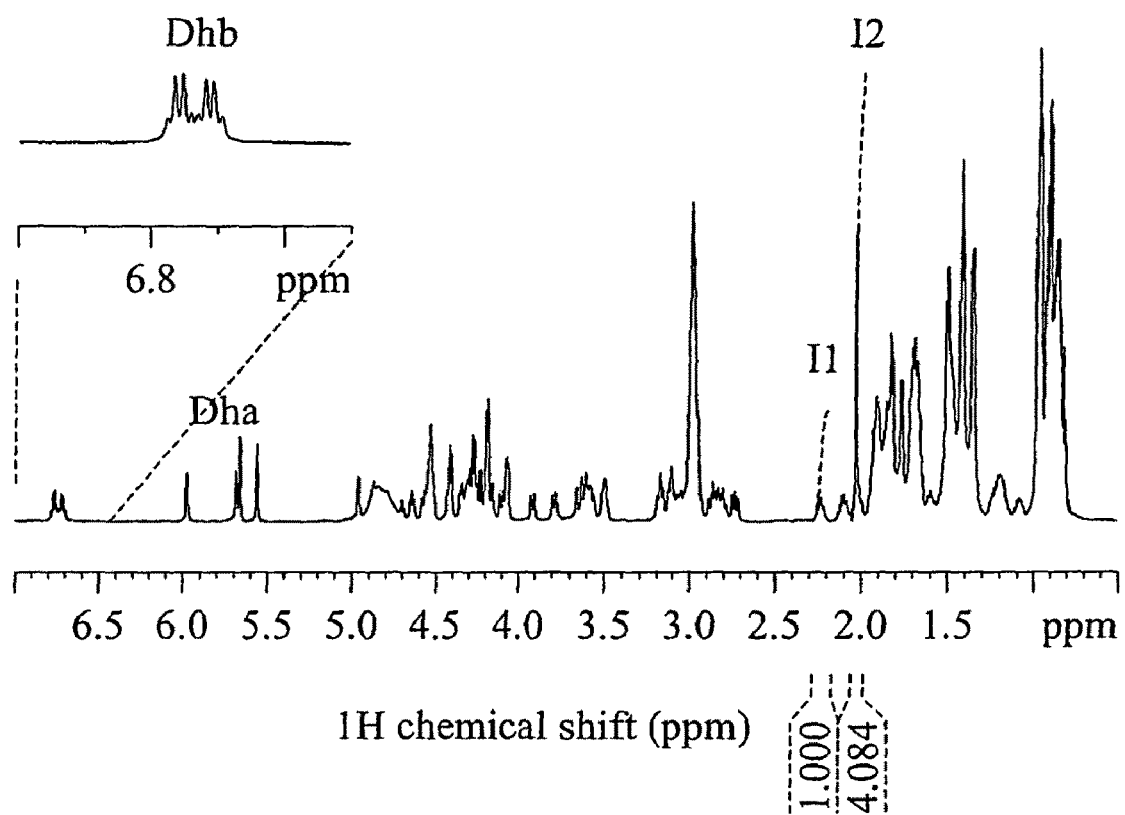

Limited NMR experiments, 1D $^1H$ NMR and 2D $^1H$ TOCSY, were conducted and described above (Examples 5 and 6) using a small amount of purified paenibacillin. With improved and larger-scale purification procedures, a total of 5.4 mg paenibacillin (white powder) was obtained, and the high purity was confirmed by SDS-PAGE and MALDI-MS analysis. The peptide powder was dissolved in $H_2O$ or $D_2O$, Systematic NMR experiments were performed and analyzed, based on previous NMR work on lantibiotics (van De Ven, F. J., and Jung, G. (1996) *Antonie Van Leeuwenhoek* 69(2), 99-107; Chan, W. C., et al. (1989) *FEBS Lett.* 252(1), 29-36; Jung, G. (1991) *Angew. Chem., Int. ed. Eng* 30, 1051-1192). Of particular note, the characteristic resonances of modified residues including A, Abu, Dha, and Dhb have been determined, and the details dealing with a unusual N-terminus are also documented (van de Kamp, et al. (1995) *Eur J Biochem* 227(3), 757-771; van de Kamp, M., et al. (1995) *Eur J Biochem* 230(2), 587-600; Ekkelenkamp, M. B., et al. (2005) *FEBS Lett* 579(9), 1917-1922). A Dhb residue, for example, can be readily identified by its unique $H^\beta$ chemical shift (~6.70 ppm) and a specific $A_3X$ pattern of spin system (van de Kamp, et al. (1995) *Eur J Biochem* 227(3), 757-771; van de Kamp, M., et al. (1995) *Eur J Biochem* 230(2), 587-600; Wuthrich, K. (1986) *NMR of protein and Nucleic Acids*, Wiley, New York, N.Y.). As shown in FIG. 12, 1D $^1H$ NMR spectrum acquired in $D_2O$ revealed two sets of quartet peaks around 6.7 ppm. These peaks, with the fine structure due to $^3J_{H\beta H\gamma}$ splitting, are clearly indicative of Dhb residues and have been confirmed by observing the $H^\beta$—$H^\gamma$ (~1.20 ppm) through-bond correlation in the TOCSY experiment (see above). The four peaks visible between 5.3 to 6.2 ppm can be candidates of $H^{\beta1,\beta2}$ protons of Dha residues, a tentative assignment that was further investigated. As no peaks were observed further downfield (e.g. >6.8 ppm), it is apparent that there is no aromatic residue present in paenibacillin. This conclusion, supported by a subsequent 2D $^1H$-$^{13}C$ HSQC experiment, facilitated the identification of alanine moiety in a Lan structure, which happens to share similar $H^{\beta1,\beta2}/C^\beta$ chemical shift ranges with those of aromatic residues, and it also simplified the interpretation of other resonances, since a ring current effect on chemical shifts can be excluded. Additional conclusions can be drawn on the basis of this simple 1D $^1H$ NMR experiment (FIG. 12). First, a clean baseline was observed around Dha and Dhb resonances, and it was estimated that the peptide preparation is >95% pure. Secondly, the spectrum recorded more than two months later did not show any noticeable changes, indicating the noteworthy stability of this lantibiotic. Finally, 1D $^1H$ NMR spectrum recorded in $H_2O$ (data not shown), shows a good chemical shift dispersion (6.8-9.8 ppm) in the amide proton region.

This noticeable chemical shift dispersion, which undoubtedly is a good sign of feasibility, was greatly beneficial in the subsequent in-depth analysis.

Amino Acid Contents Analyzed by NMR

Figure 13:
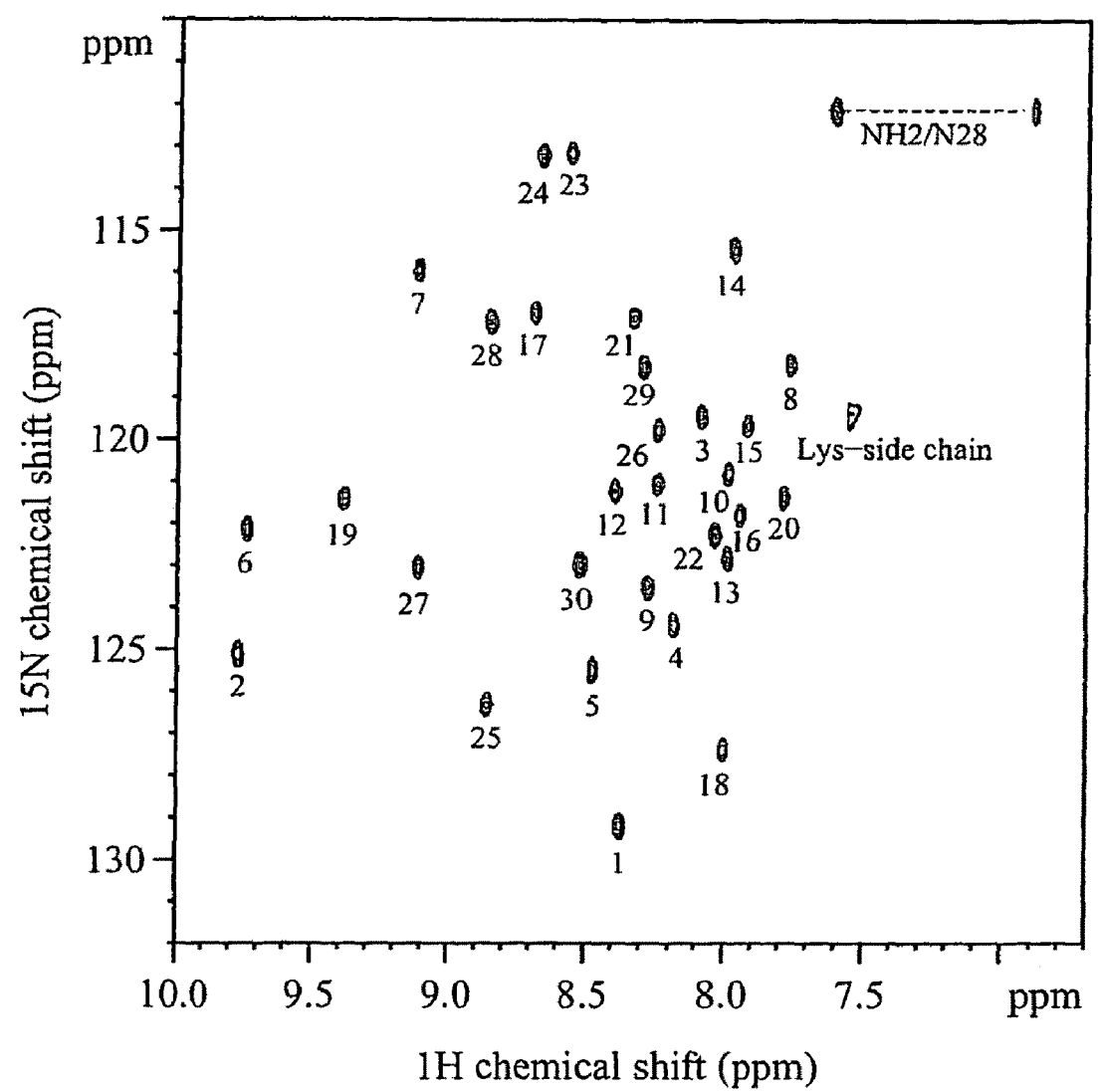
FIG. 13. 2D $^1$H-$^{15}$N HSQC recorded at 293.9 K in $H_2O$ utilizing $^{15}$N natural abundance. Peaks are labeled according to the sequential number ($CH_3CO$-$^1$A-Dha-I-I-K-Dhb-Dhb-I-K-V-A-K-A-V-A-K-Abu-L-Abu-A-I-A-Abu-G-A-A-Dha-N-A-$K^{30}$ (SEQ ID NO: 5)). The cluster peaks labeled "Lys-side chain" are aliased, attributed to the side chain amino groups of Lys residues with a $^{15}$N frequency of ~35 ppm.

2D $^1$H-$^{15}$N HSQC revealed a total of 32 unfolded cross peaks (FIG. 13), including a pair correlated with the same $^{15}$N chemical shift. The latter may be attributed to the side-chain amide group of either an Asn or a Gln residue, whereas the rest are corresponding to the backbone amides of 30 residues on a one-to-one relationship. Among these residues, presence of lysine amino acids was evident by their side-chain amino groups, which are folded into this spectrum under the current experimental setup (FIG. 13). Since the N-terminal amide proton is typically not detectable due to exchanging rapidly with water, the data suggested that this peptide comprises 31 amino acids, including an Asn or a Gln and several lysine residues.

Figure 14:
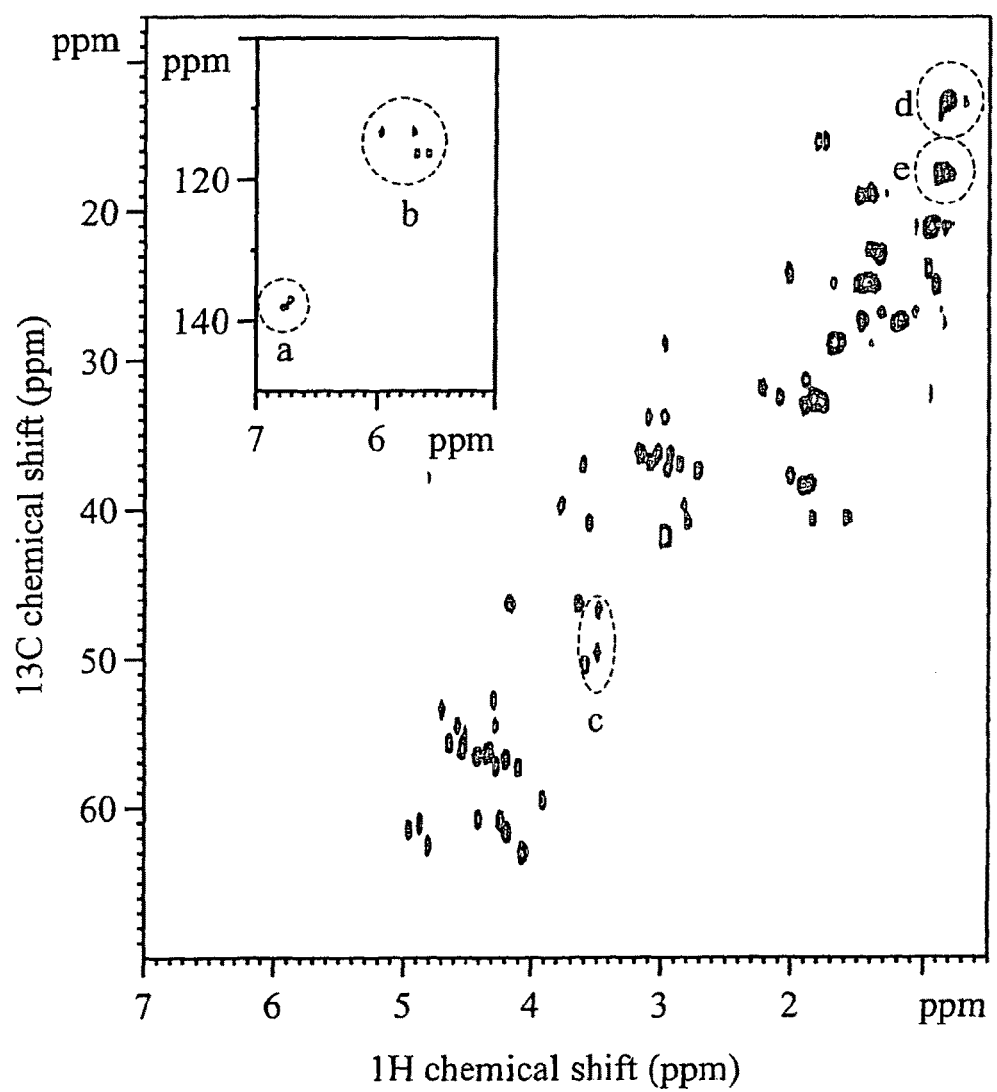
FIG. 14. 2D $^1$H-$^{13}$C HSQC recorded in $D_2O$ utilizing natural $^{13}$C abundance. The cross peaks circled and labeled by "a", "b", "c", "d" and "e" are attributed to $CH^\beta$/Dhb, $CH_2^\beta$/Dha, $CH^\beta$/Abu, $CH_3^{\delta1}$/Ile, and $CH_3^{\gamma2}$/Ile, respectively.
Figure 15:
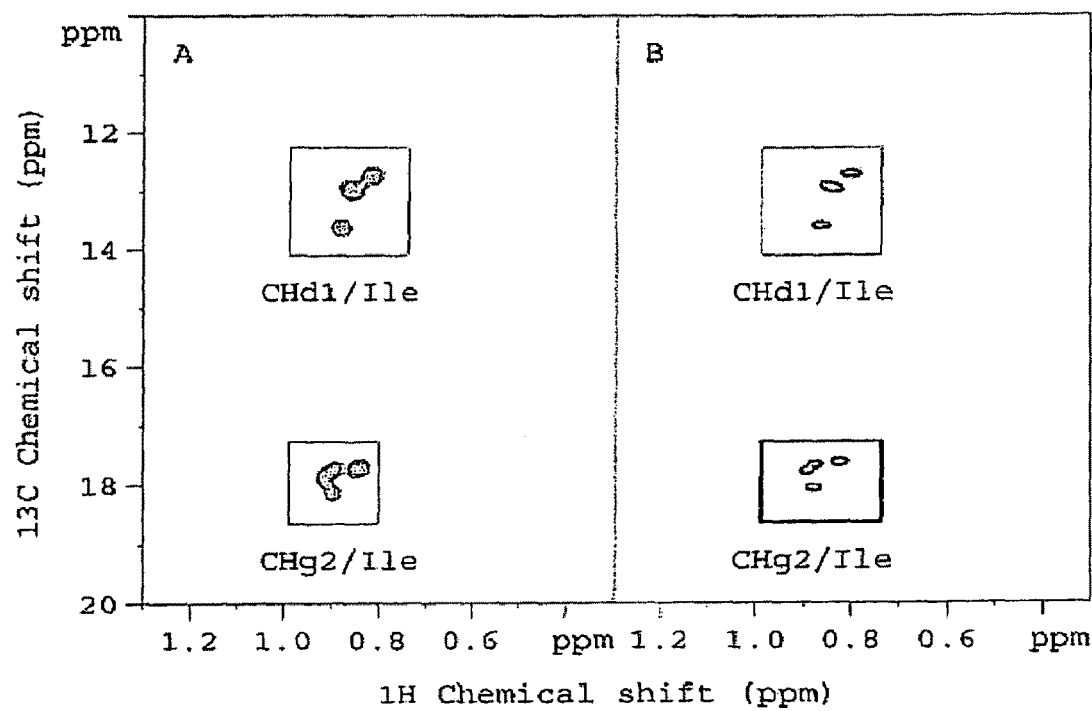
FIG. 15: (A) 2D $^1$H-$^{13}$C HSQC showing the upfield region. (B) 2D $^1$H-$^{13}$C HSQC with higher resolution, in which four Ile residues can be readily identified from $CH_3^{\gamma2}$/Ile resonances.

Abundant information regarding the amino acid contents was extracted from the interpretation of aliphatic side-chain $^1$H/$^{13}$C one-bond correlations in a 2D $^1$H-$^{13}$C HSQC experiment, recorded in D$_2$O. For example, the modified residues can be readily identified by their unique $^1$H/$^{13}$C cross-peaks: H$^{\beta1,\beta2}$/C$^{\beta}$ of Dha ~5.6/116 ppm, H$^{\beta}$/C$^{\beta}$ of Dhb ~6.70/130 ppm, and H$^{\beta}$/C$^{\beta}$ of Abu ~3.50/50 ppm (FIG. 14). Standard amino acids also exhibit characteristic chemical shifts (Wüthrich, K. (1986) *NMR of protein and Nucleic Acids*, Wiley, New York, N.Y.; Wishart, D. S., et al. (1995) *J Biomol NMR* 5(1), 67-81). This is exemplified by Ile residue whose CH$_3^{\delta1}$ typically has the most upfield resonances at ~0.95 ppm in $^1$H dimension and ~13 ppm in $^{13}$C dimension (FIG. 14). The presence of Ile residues in paenibacillin was further confirmed by another cluster of peaks positioned at ~0.95 ppm in $^1$H dimension and ~19 ppm in $^{13}$C dimension, presumably attributed to CH$_3^{\gamma2}$/Ile. Initially only three Ile residues could be counted on the basis of this data set, in addition to a Leu residue. With the input of MS/MS results, another $^1$H-$^{13}$C HSQC with higher resolution was recorded in the upfield region, leading to the identification of four Ile residues (FIG. 15).

Following the analysis of 2D $^1$H-$^{13}$C HSQC, the scalar or through-bond correlations of the resonances within a spin network were established via 2D $^1$H-homonuclear DQF-COSY and TOCSY and 2D $^1$H-$^{13}$C HSQC-TOCSY, all acquired in D$_2$O. The spin systems derived, such as AX of Gly and A$_3$X of Ala, taken together with the associated chemical shifts led to the identification of the following residues: 2 Dha, 2 Dhb, 3 Abu, 7 A, 2 Ala, 1 Asn, 1 Gly, 4 Ile, 1 Leu, 5 Lys, and 2 Val. The observation of four dehydrated amino acids is in agreement with the previous MS/MS results of isotope-induced mass shift (Examples 5 and 6, Martin, N. I., et al. (2004) *Biochemistry* 43(11), 3049-3056), although a Dha residue (Dha2) was inconclusive as discussed previously.

Figure 16:
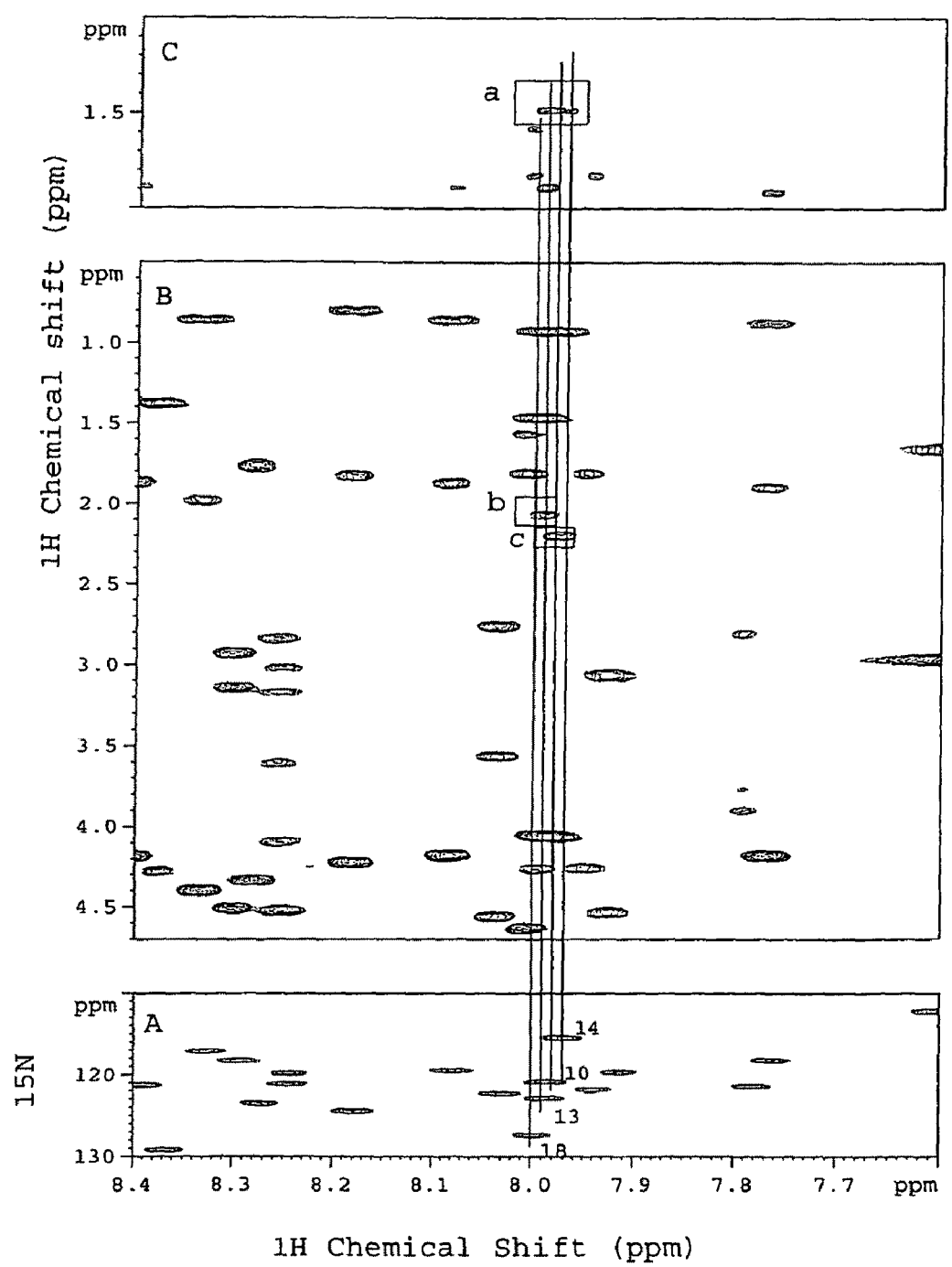
FIG. 16: (A) 2D $^1$H-$^{15}$N HSQC with the cross-peaks of V10, A13, V13, and L18 labeled. (B) 2D TOCSY showing that V13 (box b) is easily distinguished from V10 (box c) by $H^\beta$ chemical shift. (C) 2D NOESY showing the A13-V14 sequential assignment: $H^\beta$/A13-$H^N$/A13 and $H^\beta$/A13-$H^N$/V14 are boxed (box a).

The total assignment of each residue was then completed by observation of relayed scalar connectivity from the side-chain aliphatic protons to their backbone amide protons via analysis of 2D DQF-COSY and TOCSY recorded in H$_2$O. During this process, the 2D $^1$H-$^{15}$N HSQC served as a reference spectrum in resolving overlapped amide proton resonances, e.g., the four residues (V10, A13, V14 and L18) in the spectral region between 7.97 and 8.00 ppm of $^1$H dimension (FIG. 16).

Sequencing Analysis and Identification of Bridging Pattern

Figure 17:
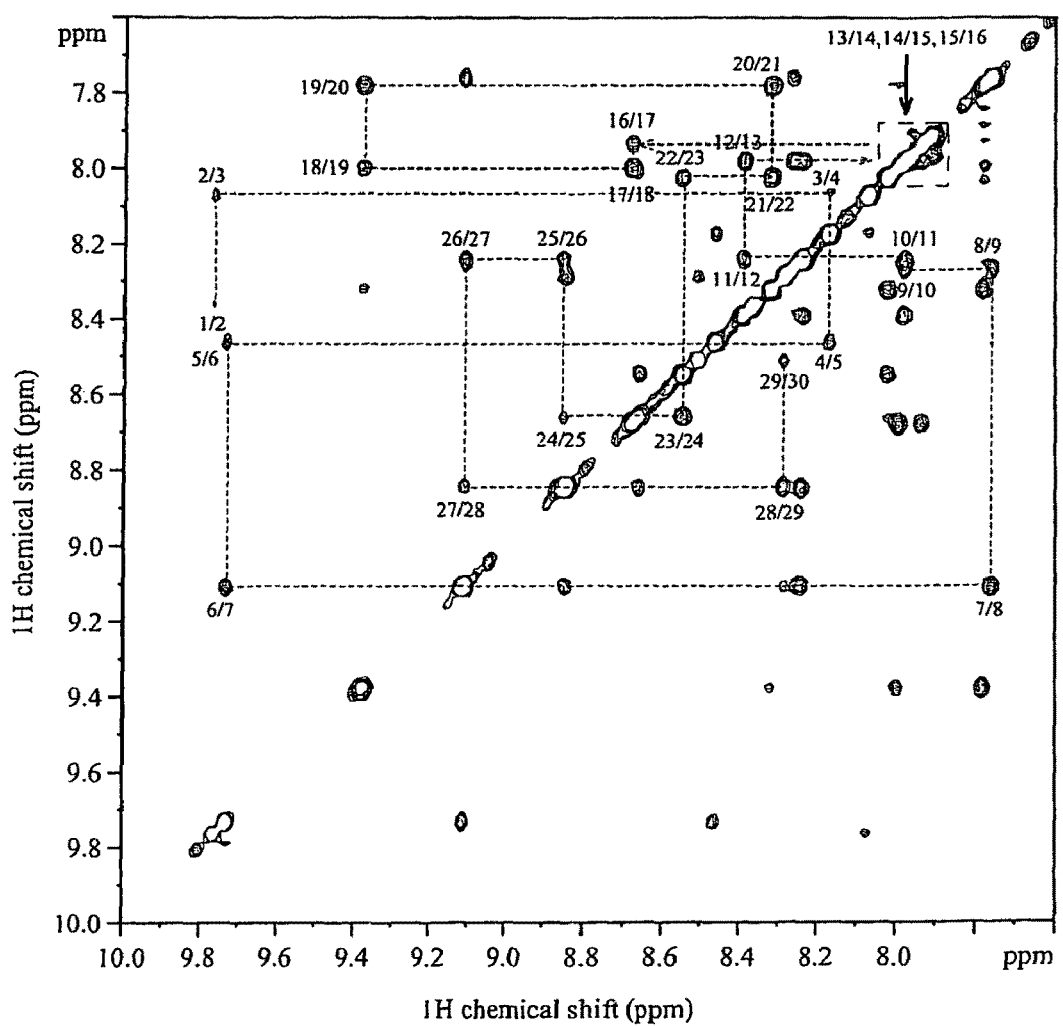
FIG. 17. Amide proton region of 2D NOESY ($\tau_m$=450 ms) recorded in $H_2O$. The $H^N$(i)–$H^N$(i+1) NOE walk along the polypeptide chain is marked with dashed line. The sequential numbers of the residues involved in a NOE interaction are labeled for each cross-peak.

The sequential assignment was carried out using through-space NOE connectivity involving side chain and backbone amide protons. As illustrated in FIG. 17, all but few (i.e., A13-K16 stretch) of the H$^N$(i)–H$^N$(i+1) NOEs throughout the sequence are well resolved in the 2D NOESY recorded in H$_2$O at 293.9K. The problems caused by the H$^N$ resonance overlap, e.g., between Dhb7 and Dha27, and between A25 and N28, (FIG. 13), were alleviated by repeating a parallel data set of 2D TOCSY, NOESY and $^1$H-$^{15}$N HSQC at a different temperature (287.3 and 301.8 K). The assignment of A13-K16 stretch, somewhat guided by MS/MS results, was achieved by the side-chain (H$^\alpha$, H$^\beta$, etc.)—backbone (H$^N$) sequential NOE assignments. For example, the A13-V14 connectivity was established by observing a distinct sequential NOE between H$^\beta$/A13 and H$^N$/V14 after reprocessing the data with different window functions for higher resolution (FIG. 16). These analyses led to the completion of the amino acid sequence, with exception of a putative residue N-terminal to A1. As summarized in Table 4, virtually all expected proton resonances have been assigned, and values are generally close to random-coil values for the natural amino acids or to what have been reported for the modified residues.

TABLE 4

Chemical shift assignments of paenibacillin in aqueous solution at pH 4.5, 293.7 K

| Residue (SEQ ID NO: 5) | $^1$H$^N$/$^{15}$N | $^1$H$^\alpha$/$^{13}$C$^\alpha$ (ppm) | $^1$H$^\beta$/$^{13}$C$^\beta$ (ppm) | Others $^1$H/$^{13}$C ($^{15}$N) (ppm) |
|---|---|---|---|---|
| CH$_3$—CO | | | 2.02/24.3 | C' 176.6 |
| A1 | 8.36/129.10 | 4.28/52.8 | 1.40/18.9 | C' 177.1 |
| Dha2 | 9.76/125.06 | —/137.8 | 5.66, 5.55/116.3 | C' 169.3 |
| I3 | 8.08/119.40 | 4.18/61.6 | 1.89/38.5 | C' 175.9 |
| | | | | H$^{\gamma1}$ 1.18/27.5 |
| | | | | H$^{\gamma2}$ 0.90/17.6 |
| | | | | H$^{\delta1}$ 0.85/12.8 |
| I4 | 8.17/124.38 | 4.22/60.9 | 1.85/38.3 | C' 176.2 |
| | | | | H$^{\gamma1}$ 1.16, 1.47/27.4 |
| | | | | H$^{\gamma2}$ 0.83/17.5 |
| | | | | H$^{\delta1}$ 0.81/12.6 |
| K5 | 8.47/125.45 | 4.41/56.6 | 1.90, 1.82/33.2 | C' 176.3 |
| | | | | H$^\gamma$ 1.50, 1.42/24.9 |
| | | | | H$^\delta$ 1.68/29.0 |
| | | | | H$^\epsilon$ 2.98/41.9 |
| Dhb6 | 9.73/122.09 | —/130.4 | 6.70/136.9 | C' 169.0 |
| | | | | H$^{\gamma1}$ 1.81/15.4 |
| Dhb7 | 9.11/115.94 | —/130.3 | 6.77/137.9 | C' 168.9 |
| | | | | H$^{\gamma1}$ 1.75/15.4 |

TABLE 4-continued

Chemical shift assignments of paenibacillin in aqueous solution at pH 4.5, 293.7 K

| Residue (SEQ ID NO: 5) | $^1H^N/^{15}N$ | $^1H^\alpha/^{13}C^\alpha$ (ppm) | $^1H^\beta/^{13}C^\beta$ (ppm) | Others $^1H/^{13}C$ ($^{15}N$) (ppm) |
|---|---|---|---|---|
| I8 | 7.76/118.17 | 4.18/61.6 | 1.90/38.4 | $H^{\gamma1}$ 1.48, 1.19/27.4 $H^{\gamma2}$ 0.90/17.6 $H^{\delta1}$ 0.85/12.8 |
| K9 | 8.27/123.46 | 4.30/56.3 | 1.78/32.8 | C' 176.2 $H^\gamma$ 1.45, 1.38/25.0 $H^\delta$ 1.63/28.9 $H^\epsilon$ 2.98/41.9 |
| V10 | 7.98/120.78 | 4.05/63.0 | 2.09/32.5 | $H^{\gamma1,\gamma2}$ 0.94/~21.2 |
| AlaS*11 | 8.24/121.01 | 4.54/56.2 | 3.18, 3.03/36.2 | |
| K12 | 8.39/121.18 | 4.18/56.8 | 1.88/31.5 | C' 176.3 $H^\gamma$ 1.44, 1.34/25.0 $H^\delta$ 1.65/28.9 $H^\epsilon$ 2.99/41.9 |
| A13 | 7.98/122.82 | 4.26/54.5 | 1.49/19.1 | C' 178.0 |
| V14 | 7.97/115.44 | 4.06/63.0 | 2.22/31.9 | C' 175.9 $H^{\gamma1,\gamma2}$ 0.95/~21.2 |
| AlaS*15 | 7.91/119.62 | 4.55/55.8 | 3.08, 3.08/37.0 | C' 174.2 |
| K16 | 7.94/121.75 | 4.26/57.2 | 1.82/32.5 | $H^\gamma$ 1.46, 1.37/25.0 $H^\delta$ 1.68/29.0 $H^\epsilon$ 2.97/41.9 |
| Abu17 | 8.68/116.96 | 4.94/61.4 | 3.59/50.3 | C' 175.2 $H^{\gamma1}$ 1.34/23.2 |
| L18 | 7.99/127.30 | 4.63/55.6 | 1.83, 1.59/40.6 | $H^\gamma$ 1.50/27.3 $H^{\delta1,\delta2}$ 0.97/24.0; 0.91/25.0 |
| Abu19 | 9.37/121.36 | 4.80/62.4 | 3.48/46.7 | C' 175.2 $H^{\gamma1}$ 1.41/22.8 |
| AlaS20 | 7.78/121.33 | 3.90/59.5 | 3.76, 2.82/39.7 | C' 175.1 |
| I21 | 8.32/117.07 | 4.40/60.8 | 2.00/37.8 | C' 175.2 $H^{\gamma1}$ 1.33, 1.08/26.9 $H^{\gamma2}$ 0.89/17.9 $H^{\delta1}$ 0.87/13.5 |
| AlaS22 | 8.03/122.24 | 4.57/54.6 | 3.56, 2.80/40.8 | |
| Abu23 | 8.55/113.12 | 4.86/61.0 | 3.48/49.6 | $H^{\gamma1}$ 1.34/22.7 |
| G24 | 8.66/113.18 | 4.16, 3.64/46.3 | | |
| AlaS*25 | 8.85/126.25 | 4.53/56.2 | 3.11, 2.97/33.8 | |
| AlaS26 | 8.24/119.74 | 4.09/57.3 | 3.62, 2.85/37.0 | C' 173.3 |
| Dha27 | 9.11/123.00 | —/136.7 | 5.96, 5.68/113.2 | C' 168.3 |
| N28 | 8.84/117.18 | 4.69/53.4 | 2.95, 2.72/37.4 | $C^\gamma$ 177.9 $NH^{\delta21}$ 7.60/112.13 $NH^{\delta22}$ 6.89/112.13 |
| AlaS*29 | 8.29/118.22 | 4.53/55.1 | 3.17, 2.95/36.4 | C' 174.5 |
| K30 | 8.51/122.94 | 4.33/56.4 | 1.91, 1.77/32.8 | $H^\gamma$ 1.42/25.0 $H^\delta$ 1.66/29.1 $H^\epsilon$ 2.96/41.9 |

Figure 18:
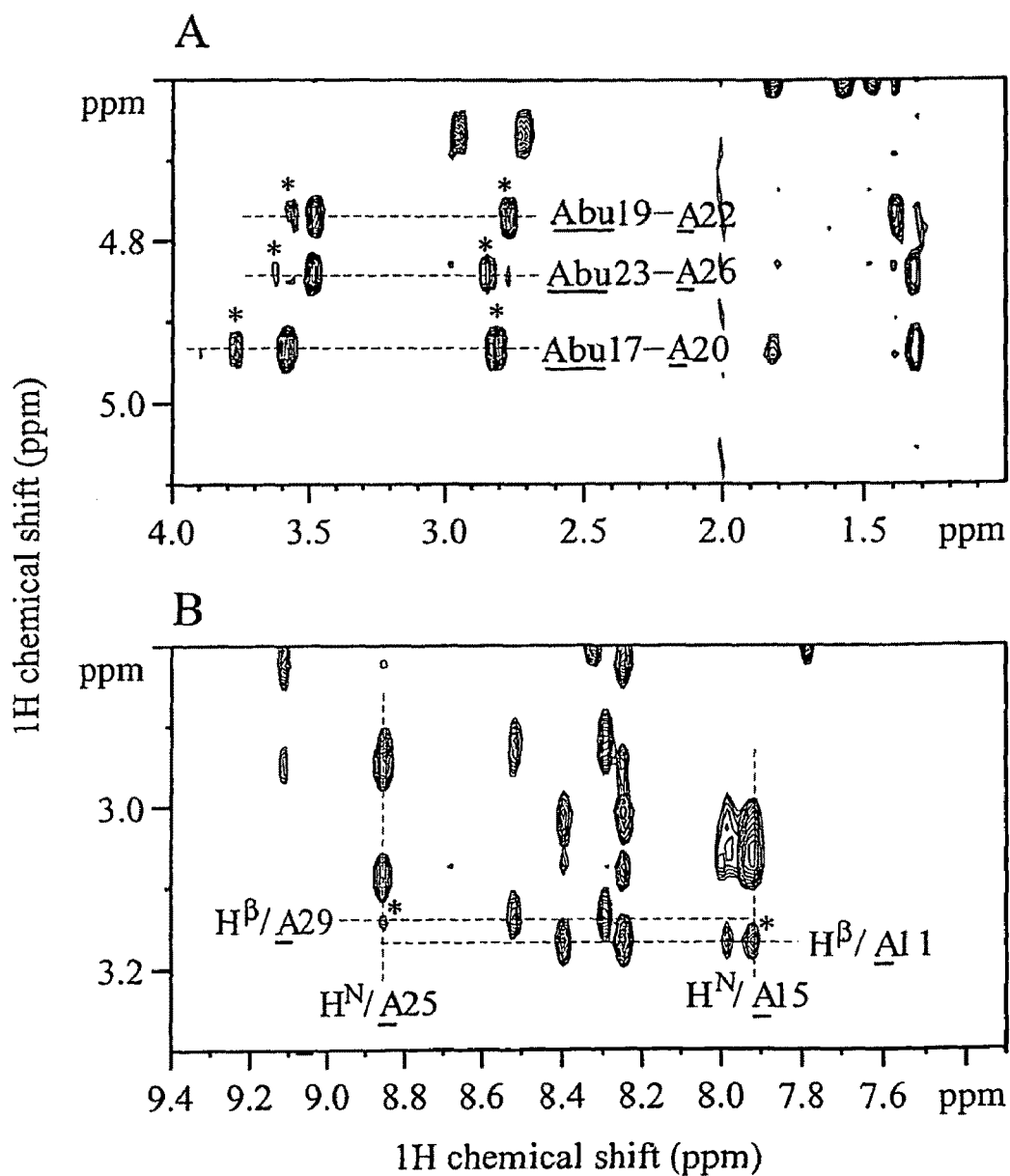
FIG. 18. NMR evidence for the thioether bridge assignments. (a) Expansion of a 2D NOESY ($\tau_m$=450 ms) recorded in $D_2O$ showing the intra-bridge NOEs, boxed, between $H^\alpha$/Abu and $H^{\beta1,\beta2}$/A in Abu-S-A MeLan structure. (b) The amide region of a 2D NOESY ($\tau_m$=450 ms) recorded in $H_2O$ showing the intra-bridge NOEs, boxed, between $H^\beta$/A11 and $H^N$/A15 and between $H^N$/A25 and $H^\beta$/A29.

Consistent with MS/MS results described above, a total of 3 Abu and 7 A residues were identified, which presumably would form two Lan and three MeLan structures. The bridging topology was deduced in this work by means of inter-residue NOE assignments across the sulfur atom. With respect to the MeLan structures, intra-bridge NOEs were identified between $H^\alpha$/Abu and $H^{\beta1,\beta2}$/A in a NOESY data set recorded in $D_2O$ (FIG. 18a). As for the Lan bridges, the spectral region for the analogous NOEs was not amenable to analysis due to serious resonance overlap (Table 4). Alternatively, the amide-aliphatic region was examined in a NOESY spectrum recorded in $H_2O$, and NOEs were observed and assigned between $H^N$ of one A moiety and $H^{\beta1,\beta2}$ across the sulfur atom (FIG. 18b). In conclusion, the following pairing pattern was firmly established: $A^{11}$-S-$A^{15}$, $Abu_{17}$-S-$A^{20}$, $Abu^{19}$-S-$A^{22}$, $Abu^{23}$-S-$A^{26}$, and $A^{25}$-S-$A^{29}$. Considering that these structural entities account for half of the residues in the A11-K30 stretch, and that there is overlap between the second and third as well as between the fourth and fifth cyclic rings, it is expected that the conformation of the C-terminal could be extremely rigid.

Elucidation of Unusual N-terminal Acetylation

Figure 19:
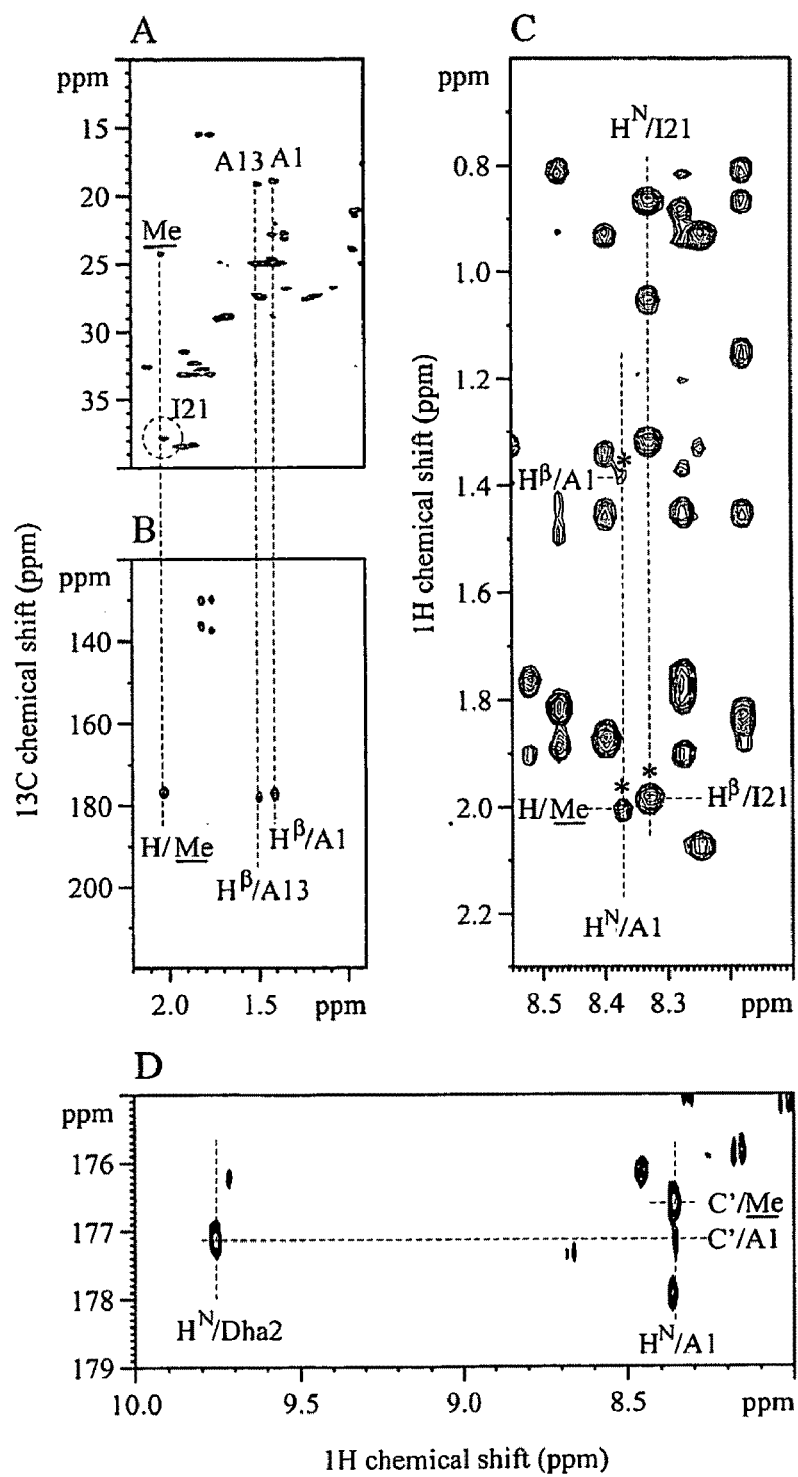
FIG. 19. NMR evidence for the assignment of N-Acetyl ($CH_3$—CO—) capping ($\underline{Me}$). (a) 2D $^1$H-$^{13}$C HSQC recorded in $D_2O$ showing unusual cross-peak at $^1H/^{13}C\sim 2.02$ ppm/ 24.3 ppm. The $CH^\beta/I21$, labeled, is the only resonance in the vicinity of the Me proton dimension within the experimental resolution. (b) 2D $^1H$-$^{13}C$ HMBC experiment optimized for long range correlation. The Me protons can be correlated to a carbonyl resonance (176.6 ppm) due to two bond or three bond J correlation, in analogy to the methyl protons of A1 and A13. (c) 2D NOESY recorded in $H_2O$ with 450 ms mixing time. A NOE was assigned between this Me and $H^N/A1$, indicating the spatial proximity of these two groups.

The previously discussed experiments did not reveal the nature of the N-terminal residue of paenibacillin. Thirty amino acids have been accounted for, but a total of 31 residues were expected. Additionally, there is a discrepancy between the experimental mass and the sum of A1-K30 fragment. In the 2D $^1H$-$^{13}C$ HSQC, all of the signals, whether resolved or overlap, have been appropriately assigned, except one resonating at 2.02 ppm in $^1H$ dimension and 24.3 ppm in $^{13}C$ dimension (FIG. 19a). The latter does not fall into any characteristic aliphatic region that belongs to either a naturally occurring amino acid or one of the dehydrated and thioether residues. First, this peak was determined to be a methyl group moiety (designated Me hereafter) based on the peak integration in 1D $^1H$ NMR, in which the $H^\beta$/I21 of virtually identical chemical shift has been taken into account (FIG. 12). Secondly, Me does not show any through-bond correlations to other proton spins in COSY and TOCSY experiments. This is even manifested in the simple 1D $^1H$ NMR (FIG. 10), as no J splitting is discernable for the sharp peak at 2.02 ppm, which is dominated by the contribution of Me over H$^\beta$/I21. The absence of scalar correlations suggests that Me behaves like an isolated spin system, which is reminiscent of an Oxp group (FIG. 10). Thirdly, like Oxp, 2D $^1$H-$^{13}$C HMBC acquired in D$_2$O revealed a through-bond correlation of $^1$H/Me to a carbonyl $^{13}$C' spin, most likely separated by two bonds (FIG. 19*b*). However, the 176.6 ppm of $^{13}$C' apparently differs from the value reported for a diketon such as 200.4 ppm in Oxp (van de Kamp, M., et al. (1995) *Eur J Biochem* 227(3), 757-771), and in fact the chemical shift is typical of a regular peptide bond ($^{13}$C'~176 ppm). Lastly, a sizable NOE was observed between $^1$H/Me and the backbone amide proton of A1 (FIG. 19*c*), indicating their spatial proximity and possible sequential relationship. The latter was unequivocally confirmed by repeating 2D $^1$H-$^{13}$C HMBC on the sample dissolved in H$_2$O. As shown in FIG. 19*d*, a sequential inter-residue two-bond $^{13}$C'(i)-$^1$H$^N$(i+1) correlation was clearly observed between the aforementioned $^{13}$C'/Me resonance (~176.6 ppm) and $^1$H$^N$/A1. Aided by the mass measurement, it is convincingly concluded that Me is just part of an acetyl group (CH$_3$—CO—), which functions exactly as the N-terminal capping to the sequence. As a final proof, a commercial sample of N-Acetyl-L-alanine was subjected to the same 2D $^1$H-$^{13}$C HSQC and $^1$H-$^{13}$C HMBC investigations. Virtually, identical chemical shifts ($^1$H/$^{13}$C/$^{13}$C'~2.00/24.5/176.0 ppm) were observed for each corresponding spin of the acetyl group in this analogue compound (data not shown). Considering this N-terminal blockage, it is not surprising that our previous attempts to analyze the peptide by Edman degradation were unsuccessful.

There are four possible base sequences for the unmodified peptide (i.e., before post-translational modification):

I.
(SEQ ID NO: 1)
X-A-*S*-I-I-K-*T*-*T*-I-K-V-*S*-K-A-V-*C*-K-*T*-L-*T*-*C*-I-*C*-*T*-G-
*S*-*C*-S-N-*C*-K

II.
(SEQ ID NO: 2)
X-A-*S*-I-I-K-*T*-*T*-I-K-V-*S*-K-A-V-*C*-K-*T*-L-*T*-*C*-I-*C*-*T*-G-
*C*-*C*-S-N-*S*-K

III.
(SEQ ID NO: 3)
X-A-*S*-I-I-K-*T*-*T*-I-K-V-*C*-K-A-V-*S*-K-*T*-L-*T*-*C*-I-*C*-*T*-G-
*S*-*C*-S-N-*C*-K

IV.
(SEQ ID NO: 4)
X-A-*S*-I-I-K-*T*-*T*-I-K-V-*C*-K-A-V-*S*-K-*T*-L-*T*-*C*-I-*C*-*T*-G-
*C*-*C*-S-N-*S*-K

Where: "X" is the source of acetyl capping of the N-terminal. This acetyl could come from a variety of sources, thus we marked it as "X". The Italicized residues, S and T, are the sources of Dha and Dhb, respectively. The red (underlined) are the source residues involved in Lan (A-S-A) structures. The blue (double underlined) are the source residues for MeLan (Abu-S-A).

Figure 20:
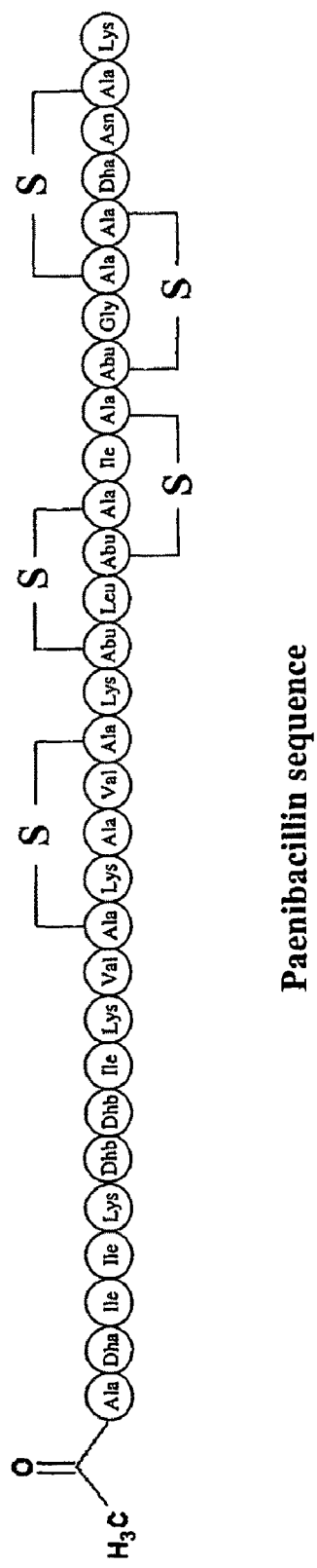
FIG. 20. Sequence of paenibacillin (SEQ ID NO: 5).
Figure 21:
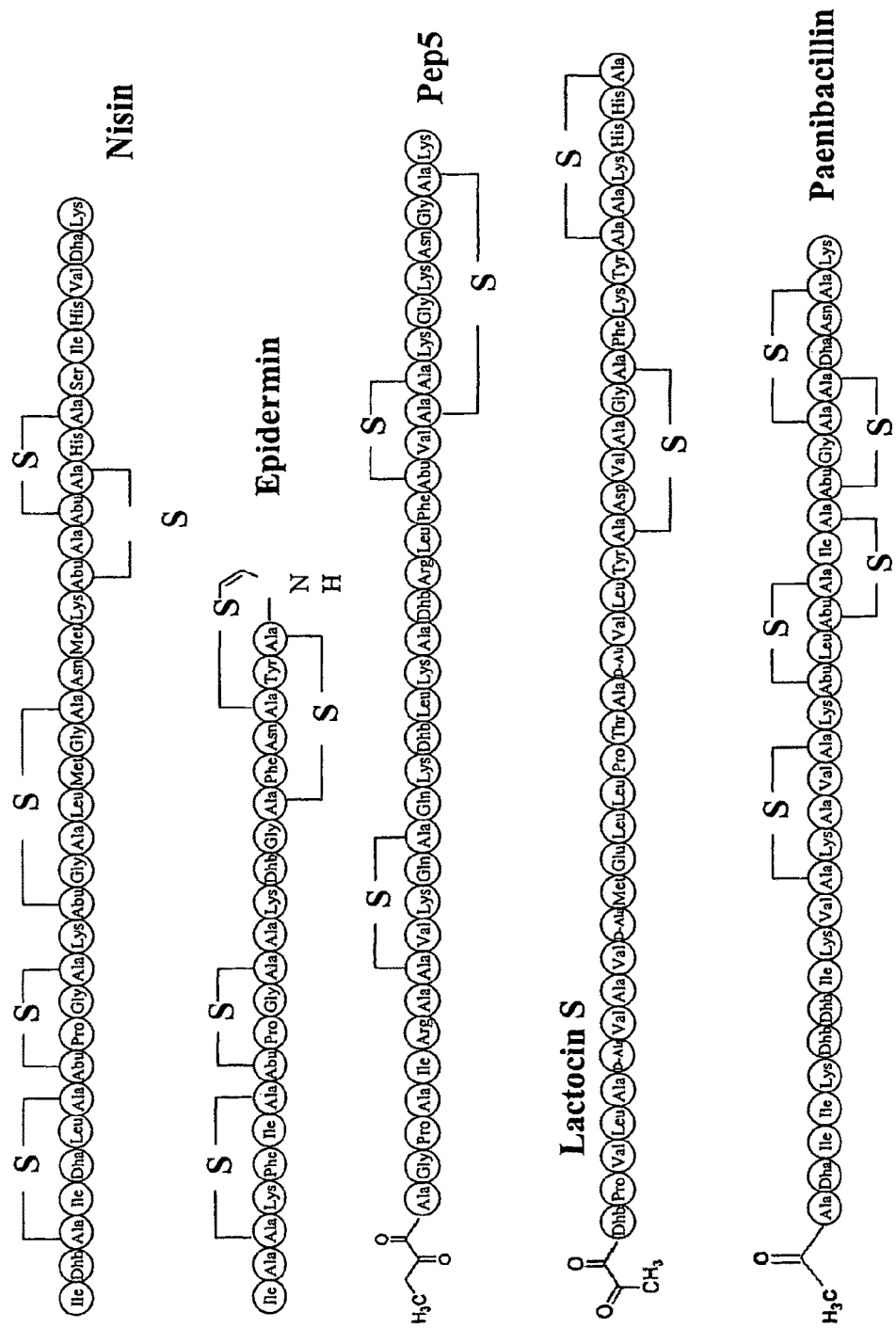
FIG. 21. Sequence comparison of paenibacillin (SEQ ID NO: 5) with other type-A lantibiotics (SEQ ID NOS 11-13, respectively, in order of appearance).

The final paenibacillin sequence is as follows: (CH$_3$ CO-$^1$A)-Dha-I-I-K-Dhb-Dhb-I-K-V-A-K-A-V-A-K-Abu-L-Abu-A-I-A-Abu-G-A-A-Dha-N-A-K$^{30}$ (SEQ ID NO: 5), in which the numbering used in this report starts at the N-acetylated alanine (FIG. 20). Results of NMR experiments are consistent with the above-described MS/MS partial sequencing. Additionally, the theoretical mass of 2983.5091 Da for the proposed sequence is identical to the observed value of 2983.53±0.1 Da.

The present invention should not be considered limited to the specific examples described above, but rather should be understood to cover all aspects of the invention. Various modifications, equivalent processes, as well as numerous structures and devices to which the present invention may be applicable will be readily apparent to those of skill in the art.

The invention claimed is:

1. An isolated peptide comprising an amino acid sequence that is at least 80% identical to the sequence SEQ ID NO.5, wherein the sequence comprises:
    (i) amino acids at positions 1, 6, 7, 11, 15, 17, 19, 20, 22, 23, 25, 26, and 29 that are identical to the amino acids in SEQ ID NO.5;
    (ii) at least four Lys residues wherein at least one of said Lys residues is at position 30;
    (iii) one or more dehydrated amino acids α,β-dehydro-alanine (Dha);
    (iv) one or more dehydrated amino acids α,β-dehydro-butyrine (Dhb); and
    (v) a Dhb-Dhb tandem,
wherein the peptide is a lantibiotic.

2. The isolated peptide of claim 1, wherein the peptide further comprises:
    one or more thioether bridges of lanthionine (Lan) between a pair of Ala-Ala residues; and
    one or more thioether bridges of β-methyllanthionine (MeLan) between a pair of Ala-Abu residues.

3. The isolated peptide of claim 2, wherein the one or more Lan bridge is present between a pair of Ala residues in positions 11 and 15, and/or between a pair of Ala residues in positions 25 and 29.

4. The isolated peptide of claim 2, wherein the one or more MeLan bridge is present between a pair of Ala-Abu residues in positions 17 and 20, and/or between a pair of Ala-Abu residues positions 19 and 22, and/or between a pair of Ala-Abu residues positions 23 and 26.

5. The isolated peptide of claim 2, wherein the N-terminus amino acid is acetylated.

6. The isolated peptide of claim 2, wherein the peptide is capable of inhibiting the growth or activity of a Gram-positive bacterium selected from *Bacillus* spp., *Clostridium sporogenes*, *Lactobacillus* spp., *Lactococcus lactis*, *Leuconostoc mesenteroides*, *Listeria* spp., *Pediococcus cerevisiae*, *Staphylococcus aureus*, *Streptococcus agalactiae* or combinations thereof.

7. The isolated peptide of claim 2, wherein the peptide comprises a sequence that is at least 90% identical to the sequence SEQ ID NO.5.

8. The isolated peptide of claim 2, wherein the peptide comprises a sequence that is at least 95% identical to the sequence SEQ ID NO.5.

9. The isolated peptide of claim 2, wherein the peptide has a sequence that is 100% identical to SEQ ID NO.5, and comprises:
    Lan bridges between a pair of Ala residues in positions 11 and 15, and between a pair of Ala residues in positions 25 and 29;
    MeLan bridges between a pair of Ala-Abu residues in positions 17 and 20, between a pair of Ala-Abu residues in positions 19 and 22, and between a pair of Ala-Abu residues in positions 23 and 26; and
    an acetylated Lys in the N-terminus.

10. An isolated precursor peptide for producing the peptide of claim 1, said precursor peptide comprising a sequence that is at least 80% identical to SEQ ID NO.1, SEQ ID NO.2, SEQ ID NO.3, or SEQ ID NO.4.

11. A method of preventing or treating a Gram-positive bacterial infection in a subject comprising administering to said subject an effective amount of a composition comprising a peptide, wherein said peptide is a lantibiotic comprising an amino acid sequence that is at least 80% identical to the sequence SEQ ID NO.5, wherein the sequence comprises:
(i) amino acids at positions 1, 6, 7, 11, 15, 17, 19, 20, 22, 23, 25, 26, and 29 that are identical to the amino acids in SEQ ID NO.5;
(ii) at least four Lys residues wherein at least one of said Lys residues is at position 30;
(iii) one or more dehydrated amino acids α,β-dehydroalanine (Dha);
(iv) one or more dehydrated amino acids α,β-dehydrobutyrine (Dhb); and
(v) a Dhb-Dhb tandem.

12. The method of claim 11, wherein the peptide further comprises:
one or more thioether bridges of lanthionine (Lan) between a pair of Ala-Ala residues; and
one or more thioether bridges of β-methyllanthionine (MeLan) between a pair of Ala Abu residues.

13. The method of claim 11, wherein the peptide has a sequence that is 100% identical to SEQ ID NO.5, and further comprises:
Lan bridges between a pair of Ala residues in positions 11 and 15, and between a pair of Ala residues in positions 25 and 29;
MeLan bridges between a pair of Ala-Abu residues in positions 17 and 20, between a pair of Ala-Abu residues in positions 19 and 22, and between a pair of Ala-Abu residues in positions 23 and 26; and
an acetylated Lys in the N-terminus.

14. The method of claim 11, wherein the bacterial infection is caused by one or more Gram-positive bacteria selected from: *Bacillus* spp., *Clostridium sporogenes, Lactobacillus* spp., *Lactococcus lactis, Leuconostoc mesenteroides, Listeria* spp., *Pediococcus cerevisiae, Staphylococcus aureus, Streptococcus agalactiae* or combinations thereof.

15. A method for preventing or inhibiting the growth of Gram-positive bacteria on or inside an environment, comprising contacting said environment with an effective amount of a composition comprising a peptide; wherein said peptide is a lantibiotic comprising an amino acid sequence that is at least 80% identical to the sequence SEQ ID NO.5, wherein the sequence comprises:
(i) amino acids at positions 1, 6, 7, 11, 15, 17, 19, 20, 22, 23, 25, 26, and 29 that are identical to the amino acids in SEQ ID NO.5;
(ii) at least four Lys residues wherein at least one of said Lys residues is at position 30;
(iii) one or more dehydrated amino acids α,β-dehydroalanine (Dha);
(iv) one or more dehydrated amino acids α,β-dehydrobutyrine (Dhb); and
(v) a Dhb-Dhb tandem.

16. The method of claim 15, wherein the peptide further comprises:
one or more thioether bridges of lanthionine (Lan) between a pair of Ala-Ala residues; and
one or more thioether bridges of β-methyllanthionine (MeLan) between a pair of Ala Abu residues.

17. The method of claim 15, wherein the peptide has a sequence that is 100% identical to SEQ ID NO.5, and further comprises:
Lan bridges between a pair of Ala residues in positions 11 and 15, and between a pair of Ala residues in positions 25 and 29;
MeLan bridges between a pair of Ala-Abu residues in positions 17 and 20, between a pair of Ala-Abu residues in positions 19 and 22, and between a pair of Ala-Abu residues in positions 23 and 26; and
an acetylated Lys in the N-terminus.

18. The method of claim 15, wherein the environment is selected from an organism, a food product, an agricultural crop, and a non-biological surface.

19. The method of claim 15, wherein the bacteria whose growth is to be prevented or inhibited comprise a Gram-positive bacterium selected from: *Bacillus* spp., *Clostridium sporogenes, Lactobacillus* spp., *Lactococcus lactis, Leuconostoc mesenteroides, Listeria* spp., *Pediococcus cerevisiae, Staphylococcus aureus, Streptococcus agalactiae* or combinations thereof.

* * * * *

SEQUENCE LISTING

<160> NUMBER OF SEQ ID NOS: 13

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Ile Ile Lys Thr Thr Ile Lys Val Ser Lys Ala Val Cys Lys
 1               5                  10                  15

Thr Leu Thr Cys Ile Cys Thr Gly Ser Cys Ser Asn Cys Lys
            20                  25                  30

<210> SEQ ID NO 2
<211> LENGTH: 30
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 2

Ala Ser Ile Ile Lys Thr Thr Ile Lys Val Ser Lys Ala Val Cys Lys
 1               5                  10                  15

Thr Leu Thr Cys Ile Cys Thr Gly Cys Cys Ser Asn Ser Lys
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Ile Ile Lys Thr Thr Ile Lys Val Cys Lys Ala Val Ser Lys
 1               5                  10                  15

Thr Leu Thr Cys Ile Cys Thr Gly Ser Cys Ser Asn Cys Lys
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Ile Ile Lys Thr Thr Ile Lys Val Cys Lys Ala Val Ser Lys
 1               5                  10                  15

Thr Leu Thr Cys Ile Cys Thr Gly Cys Cys Ser Asn Ser Lys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dehydro-alanine
<220> FEATURE:
<221> NAME/KEY: MOD_RES
<222> LOCATION: (6)..(7)
<223> OTHER INFORMATION: Dehydro-butyrine
<220> FEATURE:
<221> NAME/KEY: MOD_RES
<222> LOCATION: (17)
<223> OTHER INFORMATION: Abu
<220> FEATURE:
<221> NAME/KEY: MOD_RES
<222> LOCATION: (19)
<223> OTHER INFORMATION: Abu
<220> FEATURE:
<221> NAME/KEY: MOD_RES
<222> LOCATION: (23)
<223> OTHER INFORMATION: Abu
<220> FEATURE:
<221> NAME/KEY: MOD_RES
<222> LOCATION: (27)
<223> OTHER INFORMATION: Dehydro-alanine
```

```
<400> SEQUENCE: 5

Ala Xaa Ile Ile Lys Xaa Xaa Ile Lys Val Ala Lys Ala Val Ala Lys
 1               5                  10                  15

Xaa Leu Xaa Ala Ile Ala Xaa Gly Ala Ala Xaa Asn Ala Lys
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (3)..(4)
<223> OTHER INFORMATION: Ile or Leu
<220> FEATURE:
<221> NAME/KEY: MOD_RES
<222> LOCATION: (5)
<223> OTHER INFORMATION: Lys or Gln
<220> FEATURE:
<221> NAME/KEY: MOD_RES
<222> LOCATION: (6)..(7)
<223> OTHER INFORMATION: Abu
<220> FEATURE:
<221> NAME/KEY: MOD_RES
<222> LOCATION: (8)
<223> OTHER INFORMATION: Leu or Ile
<220> FEATURE:
<221> NAME/KEY: MOD_RES
<222> LOCATION: (9)
<223> OTHER INFORMATION: Lys or Gln
<220> FEATURE:
<221> NAME/KEY: MOD_RES
<222> LOCATION: (12)
<223> OTHER INFORMATION: Lys or Gln
<220> FEATURE:
<221> NAME/KEY: MOD_RES
<222> LOCATION: (16)
<223> OTHER INFORMATION: Lys or Gln
<220> FEATURE:
<221> NAME/KEY: MOD_RES
<222> LOCATION: (17)
<223> OTHER INFORMATION: Abu
<220> FEATURE:
<221> NAME/KEY: MOD_RES
<222> LOCATION: (18)
<223> OTHER INFORMATION: Leu or Ile
<220> FEATURE:
<221> NAME/KEY: MOD_RES
<222> LOCATION: (19)
<223> OTHER INFORMATION: Abu
<220> FEATURE:
<221> NAME/KEY: MOD_RES
<222> LOCATION: (21)
<223> OTHER INFORMATION: Leu or Ile
<220> FEATURE:
<221> NAME/KEY: MOD_RES
<222> LOCATION: (23)
<223> OTHER INFORMATION: Abu
<220> FEATURE:
<221> NAME/KEY: MOD_RES
<222> LOCATION: (30)
<223> OTHER INFORMATION: Lys or Gln

<400> SEQUENCE: 6

Xaa Xaa Xaa Xaa Xaa Xaa Xaa Xaa Xaa Val Ala Xaa Ala Val Ala Xaa
 1               5                  10                  15

Xaa Xaa Xaa Ala Xaa Ala Xaa Gly Ala Ala Ala Asn Ala Xaa
            20                  25                  30
```

```
<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(7)
<223> OTHER INFORMATION: Abu
<220> FEATURE:
<221> NAME/KEY: MOD_RES
<222> LOCATION: (17)
<223> OTHER INFORMATION: Abu
<220> FEATURE:
<221> NAME/KEY: MOD_RES
<222> LOCATION: (19)
<223> OTHER INFORMATION: Abu
<220> FEATURE:
<221> NAME/KEY: MOD_RES
<222> LOCATION: (23)
<223> OTHER INFORMATION: Abu

<400> SEQUENCE: 7

Xaa Xaa Leu Leu Lys Xaa Xaa Leu Lys Val Ala Lys Ala Val Ala Lys
 1               5                  10                  15

Xaa Leu Xaa Ala Leu Ala Xaa Gly Ala Ala Ala Asn Ala Lys
                20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (2)
<223> OTHER INFORMATION: Dehydro-alanine or dehydro-butyrine
<220> FEATURE:
<221> NAME/KEY: MOD_RES
<222> LOCATION: (3)..(4)
<223> OTHER INFORMATION: Leu or Ile
<220> FEATURE:
<221> NAME/KEY: MOD_RES
<222> LOCATION: (6)..(7)
<223> OTHER INFORMATION: Dehydro-butyrine
<220> FEATURE:
<221> NAME/KEY: MOD_RES
<222> LOCATION: (8)
<223> OTHER INFORMATION: Leu or Ile
<220> FEATURE:
<221> NAME/KEY: MOD_RES
<222> LOCATION: (17)
<223> OTHER INFORMATION: Abu
<220> FEATURE:
<221> NAME/KEY: MOD_RES
<222> LOCATION: (18)
<223> OTHER INFORMATION: Leu or Ile
<220> FEATURE:
<221> NAME/KEY: MOD_RES
<222> LOCATION: (19)
<223> OTHER INFORMATION: Abu
<220> FEATURE:
<221> NAME/KEY: MOD_RES
<222> LOCATION: (21)
<223> OTHER INFORMATION: Leu or Ile
```

```
<220> FEATURE:
<221> NAME/KEY: MOD_RES
<222> LOCATION: (23)
<223> OTHER INFORMATION: Abu
<220> FEATURE:
<221> NAME/KEY: MOD_RES
<222> LOCATION: (27)
<223> OTHER INFORMATION: Dehydro-alanine
<220> FEATURE:
<221> NAME/KEY: MOD_RES
<222> LOCATION: (30)
<223> OTHER INFORMATION: Lys or Gln

<400> SEQUENCE: 8

Xaa Xaa Xaa Xaa Lys Xaa Xaa Xaa Lys Val Ala Lys Ala Val Ala Lys
 1               5                  10                  15

Xaa Xaa Xaa Ala Xaa Ala Xaa Gly Ala Ala Xaa Asn Ala Xaa
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (6)..(7)
<223> OTHER INFORMATION: Abu
<220> FEATURE:
<221> NAME/KEY: MOD_RES
<222> LOCATION: (17)
<223> OTHER INFORMATION: Abu
<220> FEATURE:
<221> NAME/KEY: MOD_RES
<222> LOCATION: (19)
<223> OTHER INFORMATION: Abu
<220> FEATURE:
<221> NAME/KEY: MOD_RES
<222> LOCATION: (23)
<223> OTHER INFORMATION: Abu

<400> SEQUENCE: 9

Xaa Xaa Ile Ile Lys Xaa Xaa Ile Lys Val Ala Lys Ala Val Ala Lys
 1               5                  10                  15

Xaa Ile Xaa Ala Ile Ala Xaa Gly Ala Ala Ala Asn Ala Lys
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Diaminobutyric acid
<220> FEATURE:
<221> NAME/KEY: MOD_RES
<222> LOCATION: (3)..(4)
<223> OTHER INFORMATION: Diaminobutyric acid
<220> FEATURE:
<221> NAME/KEY: MOD_RES
<222> LOCATION: (6)..(7)
<223> OTHER INFORMATION: Diaminobutyric acid
```

-continued

```
<220> FEATURE:
<221> NAME/KEY: MOD_RES
<222> LOCATION: (10)
<223> OTHER INFORMATION: Diaminobutyric acid

<400> SEQUENCE: 10

Xaa Thr Xaa Xaa Thr Xaa Xaa Leu Leu Xaa
 1               5                  10

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dehydro-butyrine
<220> FEATURE:
<221> NAME/KEY: MOD_RES
<222> LOCATION: (5)
<223> OTHER INFORMATION: Dehydro-alanine
<220> FEATURE:
<221> NAME/KEY: MOD_RES
<222> LOCATION: (8)
<223> OTHER INFORMATION: Abu
<220> FEATURE:
<221> NAME/KEY: MOD_RES
<222> LOCATION: (13)
<223> OTHER INFORMATION: Abu
<220> FEATURE:
<221> NAME/KEY: MOD_RES
<222> LOCATION: (23)
<223> OTHER INFORMATION: Abu
<220> FEATURE:
<221> NAME/KEY: MOD_RES
<222> LOCATION: (25)
<223> OTHER INFORMATION: Abu
<220> FEATURE:
<221> NAME/KEY: MOD_RES
<222> LOCATION: (33)
<223> OTHER INFORMATION: Dehydro-alanine

<400> SEQUENCE: 11

Ile Xaa Ala Ile Xaa Leu Ala Xaa Pro Gly Ala Lys Xaa Gly Ala Leu
 1               5                  10                  15

Met Gly Ala Asn Met Lys Xaa Ala Xaa Ala His Ala Ser Ile His Val
            20                  25                  30

Xaa Lys

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Abu
<220> FEATURE:
<221> NAME/KEY: MOD_RES
<222> LOCATION: (14)
<223> OTHER INFORMATION: Dehydro-butyrine
```

```
<400> SEQUENCE: 12

Ile Ala Ala Lys Phe Ile Ala Xaa Pro Gly Ala Ala Lys Xaa Gly Ala
1               5                   10                  15

Phe Asn Ala Tyr Ala
            20

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Dehydro-butyrine
<220> FEATURE:
<221> NAME/KEY: MOD_RES
<222> LOCATION: (19)
<223> OTHER INFORMATION: Dehydro-butyrine
<220> FEATURE:
<221> NAME/KEY: MOD_RES
<222> LOCATION: (23)
<223> OTHER INFORMATION: Abu

<400> SEQUENCE: 13

Ala Gly Pro Ala Ile Arg Ala Ala Val Lys Gln Ala Gln Lys Xaa Leu
1               5                   10                  15

Lys Ala Xaa Arg Leu Phe Xaa Val Ala Ala Lys Gly Lys Asn Gly Ala
            20                  25                  30

Lys
```